(12) United States Patent
Goldberg et al.

(10) Patent No.: US 11,433,040 B2
(45) Date of Patent: Sep. 6, 2022

(54) METHODS FOR MODIFYING ENDOPLASMIC RETICULUM PROCESSING OF PROTEIN

(71) Applicant: MEMORIAL SLOAN KETTERING CANCER CENTER, New York, NY (US)

(72) Inventors: Jonathan Goldberg, New York, NY (US); Elena Goldberg, New York, NY (US); Wenfu Ma, New York, NY (US)

(73) Assignee: MEMORIAL SLOAN KETTERING CANCER CENTER, New York, NY (US)

( * ) Notice: Subject to any disclaimer, the term of this patent is extended or adjusted under 35 U.S.C. 154(b) by 87 days.

(21) Appl. No.: 16/614,770

(22) PCT Filed: May 18, 2018

(86) PCT No.: PCT/US2018/033382
§ 371 (c)(1),
(2) Date: Nov. 18, 2019

(87) PCT Pub. No.: WO2018/213699
PCT Pub. Date: Nov. 22, 2018

(65) Prior Publication Data
US 2020/0179316 A1 Jun. 11, 2020

Related U.S. Application Data

(60) Provisional application No. 62/508,615, filed on May 19, 2017.

(51) Int. Cl.
| | | |
|---|---|---|
| A61K 31/192 | (2006.01) | |
| A61K 31/222 | (2006.01) | |
| A61K 45/06 | (2006.01) | |
| A61P 35/00 | (2006.01) | |

(52) U.S. Cl.
CPC .......... *A61K 31/192* (2013.01); *A61K 31/222* (2013.01); *A61P 35/00* (2018.01); *A61K 45/06* (2013.01)

(58) Field of Classification Search
CPC ...... A61K 31/192; A61K 31/222; A61P 35/00
See application file for complete search history.

(56) References Cited

U.S. PATENT DOCUMENTS

| | | | | |
|---|---|---|---|---|
| 5,877,213 | A * | 3/1999 | Samid .................. | A61K 31/365 514/568 |
| 2010/0093862 | A1 | 4/2010 | Torigoe et al. | |
| 2017/0007573 | A1 | 1/2017 | Nezami | |

FOREIGN PATENT DOCUMENTS

WO WO-2017/019664 A1 2/2017

OTHER PUBLICATIONS

Svechnikova et al. International Journal of Oncology, 2003, vol. 22, pp. 579-588 (Year: 2003).*
Ott et al. Journal for Immuno Therapy of Cancer, 2017, 5:16, 15 pages (Published Online Feb. 2, 2017) (Year: 2017).*
Jazirehi et al. Am. J. Cancer Res., 2016, 6(10), pp. 2117-2128 (Year: 2016).*
Bohnert et al., "Inhibition of ER stress and unfolding protein response pathways causes skeletal muscle wasting during cancer cachexia," FASEB, vol. 30, Iss. 9, pp. 3059-3068 (May 20, 2016).
Ghasemzadeh et al., "New strategies in bladder cancer: a second coming for immunotherapy," Clin. Cancer Res., vol. 22, Iss. 4, pp. 793-801 (Dec. 18, 2015).
International Search Report and Written Opinion, PCT/US2018/033382, Memorial Sloan Kettering Cancer Center (dated Sep. 21, 2018).
Do-Sung Kim et a.: The regulatory mechanism of 4-phenylbutyric acid against ER stress-induced autophagy in human gingival fibroblasts11 , Archives of Pharmacal Research, Pharmaceutical Society of Korea, Heidelberg, vol. 35, No. 7, Aug. 3, 2012 (Aug. 3, 2012), pp. 1269-1278, XP035094774, ISSN: 1976-3786, DOI: 10.1007/S12272-012-0718-2.
Lin Jianqing et al: A Phase I Dose-Finding Study of 5-Azacytidine in Combination with Sodium Phenylbutyrate in Patients with Refractory Solid Tumors11 , Clinical Cancer Research, vol. 15, No. 19, Oct. 1, 2009 (Oct. 1, 2009), pp. 6241-6249, XP002801741.
P Maslak et al: Pilot study of combination transcriptional modulation therapy with sodium phenylbutyrate and 5-azacytidine in patients with acute myeloid leukemia or myelodysplastic syndrome, Leukemia, vol. 20, No. 2, Dec. 15, 2005 (Dec. 15, 2005), pp. 212-217, XP055145127, ISSN: 0887-6924, DOI:10.1038/sj.leu.2404050.
Seisuke Mimori et al: Protective Effects of 4-Phenylbutyrate Derivatives on the Neuronal Cell Death and Endoplasmic Reticulum Stress11 , Biological & Pharmaceutical Bulletin, vol. 35, No. 1, Jan. 1, 2012 (Jan. 1, 2012), pp. 84-90, XP055340337, JP ISSN: 0918-6158, DOI: 10.1248/bpb.35.84.

(Continued)

Primary Examiner — James D. Anderson
(74) Attorney, Agent, or Firm — Foley & Lardner LLP

(57) ABSTRACT

The present disclosure provides compositions and methods for modifying endoplasmic reticulum trafficking of proteins. Also disclosed herein are methods for treating cancer and/or enhancing cancer or viral immunotherapy in a subject by increasing the extracellular secretion levels of GRP94 in the subject. Such methods comprise administering to the subject an effective amount of 4-PBA and/or a 4-PBA analog selected from among methoxy-PBA, 3-PPA, 5-PVA, hydroxy-PPA, hydroxy-PBA, and tolyl-BA.

5 Claims, 21 Drawing Sheets
Specification includes a Sequence Listing.

(56) References Cited

OTHER PUBLICATIONS

Xu Yawen et al: Sodium phenylbutyrate antagonizes prostate cancer through the induction of apoptosis and attenuation of cell viability and migration11 , Oncotargets and Therapy, vol. 9, 2016, pp. 2825-2833, XP002801740.

Lee et al., "Elevated endoplasmic reticulum stress reinforced immunosuppression in the tumor microenvironment via myeloid-derived suppressor cells." Oncotarget, vol. 5, No. 23:12331-45 (2014).

* cited by examiner

SEQUENCE LISTING

```
<160> NUMBER OF SEQ ID NOS: 15

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Val Thr Ser Leu Val
1               5

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 2

Gln Ile Tyr Thr Asp Ile Glu Ala Asn Arg
1               5                   10

<210> SEQ ID NO 3
<211> LENGTH: 4
<212> TYPE: PRT
<213> ORGANISM: Homo sapiens

<400> SEQUENCE: 3

Lys Asp Glu Leu
1
```

```
<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 4

His His His His His His
1               5

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tggtacacga caatcagtgg tcaa                                          24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cacagcacac tggattaagg ctcc                                          24

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Pro Leu Gly Ser Met Ser Phe Ile
1               5

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtcatcaccc tagatctcct cagt                                          24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
attgggccac tgaatgtttt cagt                                          24
```

```
<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Val Thr Ser Val Val
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Val Thr Ser Ile Ile
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Glu Val Thr Ser Ser Val
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Glu Val Thr Ser Phe Ala
1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Glu Val Thr Ser Phe Phe
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 15

Glu Val Thr Ser Leu Leu
1               5
```

METHODS FOR MODIFYING ENDOPLASMIC RETICULUM PROCESSING OF PROTEIN

CROSS-REFERENCE TO RELATED APPLICATIONS

This application is a National Stage Application of PCT/US2018/033382, filed May 18, 2018, which claims the benefit of and priority to U.S. Provisional Appl. No. 62/508,615, filed May 19, 2017, the disclosure of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Jul. 19, 2018, is named 115872-0364_SL.txt and is 3,391 bytes in size.

TECHNICAL FIELD

The present technology relates generally to compositions and methods for modifying endoplasmic reticulum trafficking of proteins. Also disclosed herein are methods for treating cancer and/or enhancing cancer or viral immunotherapy in a subject in need thereof comprising increasing the extracellular secretion levels of GRP94 in the subject.

BACKGROUND

The following description is provided to assist the understanding of the reader. None of the information provided or references cited is admitted to be prior art to the compositions and methods disclosed herein.

Native cargo proteins can exit the endoplasmic reticulum (ER) in COPII-coated vesicles, whereas ER resident and misfolded proteins are substantially maintained within the ER and excluded from being packaged in vesicles.

Candidate machinery for protein retention in the ER includes the p24-family proteins. These highly conserved transmembrane proteins cycle continuously between the ER and Golgi membranes as abundant constituents of COPI and COPII vesicles. Mutation of p24 genes results in post-ER trafficking of a misfolded protein in *Caenorhabditis elegans*. Deletion of p24 genes in yeast causes misfolded proteins and chaperones to escape the ER, with the latter being secreted into the extracellular medium. These effects may be attributable in part to a chronic unfolded protein response (UPR) in the knockout strains.

SUMMARY

In one aspect, the present disclosure provides a method for treating cancer in a subject in need thereof comprising administering to the subject an effective amount of 4-PBA, a compound of Formula I, and/or a 4-PBA analog selected from among methoxy-PBA, 3-PPA, 5-PVA, hydroxy-PPA, hydroxy-PBA, and tolyl-BA. 4-PBA, the compound of Formula I, and/or the 4-PBA analog is administered orally, topically, intranasally, systemically, intravenously, subcutaneously, intraperitoneally, intradermally, intraocularly, iontophoretically, transmucosally, or intramuscularly. In some embodiments, one or more cells of the subject are under endoplasmic reticulum (ER) stress. In certain embodiments, the one or more cells under ER stress are cancer cells. Additionally or alternatively, in some embodiments, the subject is human. In some embodiments, 4-PBA, the compound of Formula I, and/or the 4-PBA analog binds to COPII protein.

Additionally or alternatively, in some embodiments, the method comprises separately, sequentially or simultaneously administering one or more checkpoint inhibitors and/or one or more immune system stimulators. The one or more checkpoint inhibitors may target PD-1, PD-L1 or CTLA-4. In some embodiments, the checkpoint inhibitor is selected from the group consisting of ipilimumab, pembrolizumab, nivolumab, atezolizumab, avelumab, durvalumab, pidilizumab, AMP-224, MPDL3280A, MDX-1105, MEDI-4736, arelumab, tremelimumab, IMP321, MGA271, BMS-986016, lirilumab, urelumab, PF-05082566, IPH2101, MEDI-6469, CP-870,893, Mogamulizumab, Varlilumab, Galiximab, AMP-514, AUNP 12, Indoximod, NLG-919, INCB024360 (Incyte) and any combination thereof.

Additionally or alternatively, in some embodiments, the one or more immune system stimulators are selected from the group consisting of a natural killer cell (NK) stimulator, an antigen presenting cell (APC) stimulator, a granulocyte macrophage colony-stimulating factor (GM-CSF), and a toll-like receptor stimulator. Examples of the NK stimulator include, but are not limited to, IL-2, IL-15, IL-15/IL-15RA complex, IL-18, and IL-12, as well as an antibody that stimulates one or more receptors selected from the group consisting of NKG2, KIR2DL1/S1, KRI2DL5A, NKG2D, NKp46, NKp44, and NKp30. Examples of the APC stimulator include, but are not limited to, CD28, inducible costimulatory (ICOS), CD40, CD30, CD27, OX-40, and 4-1BB.

In any of the above embodiments of the methods disclosed herein, the cancer is bladder cancer, breast cancer, cervical cancer, colon cancer, esophageal cancer, endometrial cancer, gastric cancer, glioblastoma, head and neck cancer, hepatocellular carcinoma, leukemia, lung cancer, lymphoma, melanoma, Merkel cell carcinoma, multiple myeloma, neuroblastoma, neuroendocrine cancer, non-small cell lung cancer, ovarian cancer, pancreatic cancer, prostate cancer, rectal cancer, renal cell carcinoma, rhabdoid cancer, sarcoma, or urinary tract cancer.

Additionally or alternatively, in some embodiments, administration of 4-PBA, the compound of Formula I, and/or the 4-PBA analog results in increased GRP94 extracellular levels in the subject (e.g., at least 1.5 fold, at least 2 fold, at least 2.5 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, or at least 10 fold) compared to that observed in the subject prior to administration.

Additionally or alternatively, in some embodiments, 4-PBA, the compound of Formula I, and/or the 4-PBA analog is administered daily for 6 weeks or more. In some embodiments, 4-PBA, the compound of Formula I, and/or the 4-PBA analog is administered daily for 12 weeks or more.

In one aspect, the present disclosure provides a method for enhancing cancer immunotherapy in a subject in need thereof comprising administering to the subject an effective amount of 4-PBA, a compound of Formula I, and/or a 4-PBA analog selected from among methoxy-PBA, 3-PPA, 5-PVA, hydroxy-PPA, hydroxy-PBA, and tolyl-BA. In some embodiments, administration of 4-PBA, the compound of Formula I, and/or the 4-PBA analog results in elevated secretion of GRP94/neoantigen complexes in the subject compared to that observed in the subject prior to administration. The GRP94/neoantigen complexes may comprise neoantigenic peptides that are about 5 to about 50 amino acids in length. Additionally or alternatively, in some embodiments, the subject is diagnosed with a cancer selected from the group consisting of bladder cancer, breast cancer, cervical cancer, colon cancer, esophageal cancer, endometrial cancer, gastric cancer, glioblastoma, head and neck cancer, hepatocellular carcinoma, leukemia, lung cancer, lymphoma, melanoma, Merkel cell carcinoma, multiple myeloma, neuroblastoma, neuroendocrine cancer, non-small cell lung cancer, ovarian cancer, pancreatic cancer, prostate cancer, rectal cancer, renal cell carcinoma, rhabdoid cancer, sarcoma, and urinary tract cancer.

In another aspect, the present disclosure provides a method for enhancing viral immunotherapy in a subject in need thereof comprising administering to the subject an effective amount of 4-PBA, a compound of Formula I, and/or a 4-PBA analog selected from among methoxy-PBA, 3-PPA, 5-PVA, hydroxy-PPA, hydroxy-PBA, and tolyl-BA. In some embodiments, administration of 4-PBA, the compound of Formula I, and/or the 4-PBA analog results in elevated secretion of GRP94/viral antigen complexes in the subject compared to that observed in the subject prior to administration. Additionally or alternatively, in some embodiments, the subject is infected with a virus selected from the group consisting of human immunodeficiency virus (HIV), herpes simplex virus (HSV), influenza virus, EBV, Ebola virus, chicken pox virus, Hepatitis B virus, Hepatitis C virus, HPV, rubeola virus, rubulavirus, rubella virus, poliovirus, Rous Sarcoma Virus, rabies virus, and rotavirus.

Additionally or alternatively, in some embodiments of the methods disclosed herein, 4-PBA, the compound of Formula I, and/or the 4-PBA analog is administered orally, topically, intranasally, systemically, intravenously, subcutaneously, intraperitoneally, intradermally, intraocularly, iontophoretically, transmucosally, or intramuscularly.

In any of the foregoing embodiments, the methods of the present technology further comprise administering an effective amount of an adjuvant to the subject. Additionally or alternatively, in some embodiments, the methods further comprise separately, sequentially or simultaneously administering one or more checkpoint inhibitors disclosed herein and/or one or more immune system stimulators disclosed herein.

In one aspect, the present disclosure provides a method for increasing extracellular secretion of GRP94 by one or more cells in a subject in need thereof comprising administering to the subject an effective amount of 4-PBA, a compound of Formula I, and/or a 4-PBA analog selected from among methoxy-PBA, 3-PPA, 5-PVA, hydroxy-PPA, hydroxy-PBA, and tolyl-BA. 4-PBA, the compound of Formula I, and/or the 4-PBA analog may be administered orally, topically, intranasally, systemically, intravenously, subcutaneously, intraperitoneally, intradermally, intraocularly, iontophoretically, transmucosally, or intramuscularly. Additionally or alternatively, in some embodiments, the one or more cells are cells under ER stress.

In certain embodiments, the subject is diagnosed with or suffers from cancer. Examples of cancer include bladder cancer, breast cancer, cervical cancer, colon cancer, esophageal cancer, endometrial cancer, gastric cancer, glioblastoma, head and neck cancer, hepatocellular carcinoma, leukemia, lung cancer, lymphoma, melanoma, Merkel cell carcinoma, multiple myeloma, neuroblastoma, neuroendocrine cancer, non-small cell lung cancer, ovarian cancer, pancreatic cancer, prostate cancer, rectal cancer, renal cell carcinoma, rhabdoid cancer, sarcoma, or urinary tract cancer. Additionally or alternatively, in some embodiments, the secreted GRP94 is complexed with tumor neoantigens.

Additionally or alternatively, in some embodiments, the subject is infected with a virus. The virus may be selected from the group consisting of human immunodeficiency virus (HIV), herpes simplex virus (HSV), influenza virus, EBV, Ebola virus, chicken pox virus, Hepatitis B virus, Hepatitis C virus, HPV, rubeola virus, rubulavirus, rubella virus, poliovirus, Rous Sarcoma Virus, rabies virus, and rotavirus. Additionally or alternatively, in some embodiments, the secreted GRP94 is complexed with viral antigens.

Leu-Leu is an effective ER export motif, but not as potent as Val-Val.

Figure 7A:
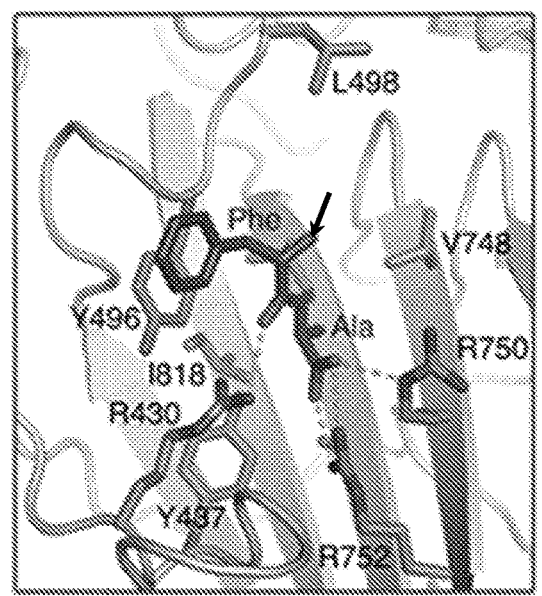
FIG. 7(A) shows a close-up view of a bound ΦC sequence containing a terminal Phe-Ala motif (black arrow). This signal accelerates ER export of a reporter protein with potency comparable to Phe-Phe. See Table 1 for details of peptide-bound crystal structures.
Figure 7B:
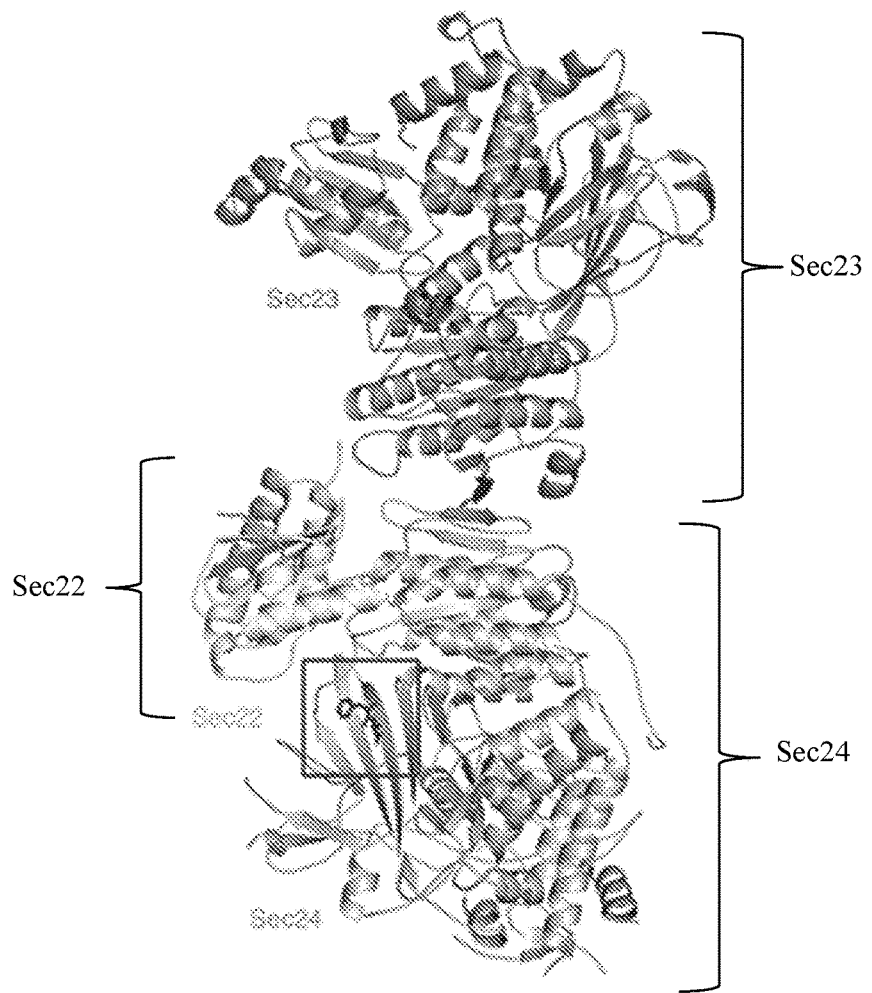
FIG. 7(B) shows the structure of the COPII complex comprising human Sec23a/Sec24a•Sec22b bound to a ΦC peptide (boxed).
Figure 7C:
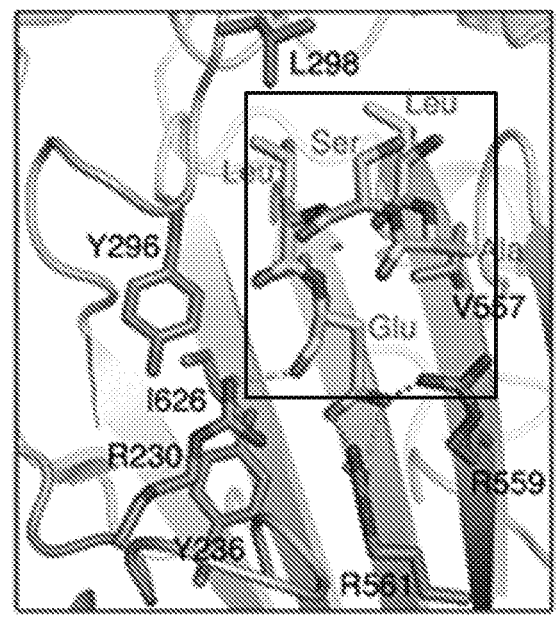
FIG. 7(C) shows the binding site of S. cerevisiae Sec24 bound to the LxxLE motif of the SNARE protein Bet1 (boxed); from Mossessova et al., Cell 114, 483-495 (2003).
Figure 7D:
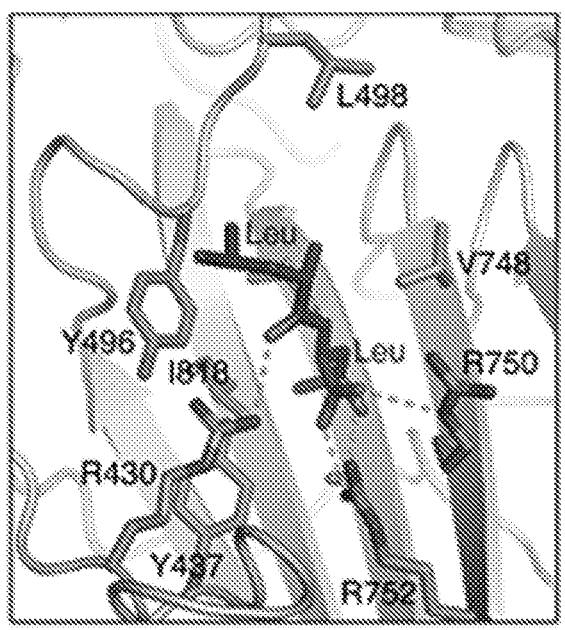
FIG. 7(D) shows a bound ΦC sequence containing a terminal Leu-Leu motif.
Figure 7E:
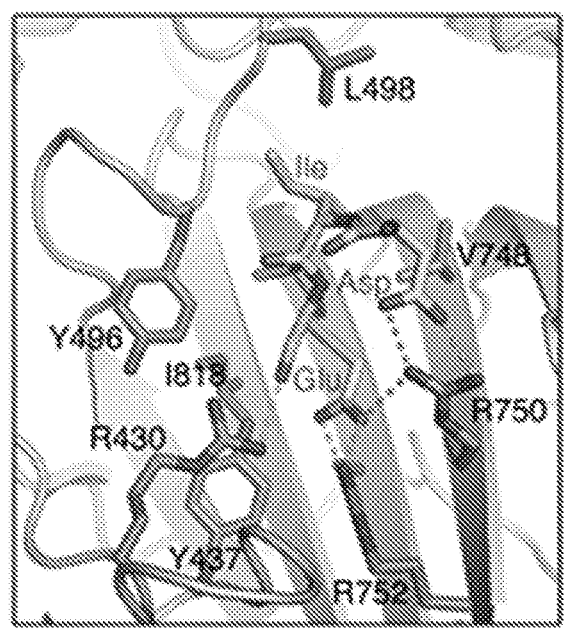
Figure 7F:
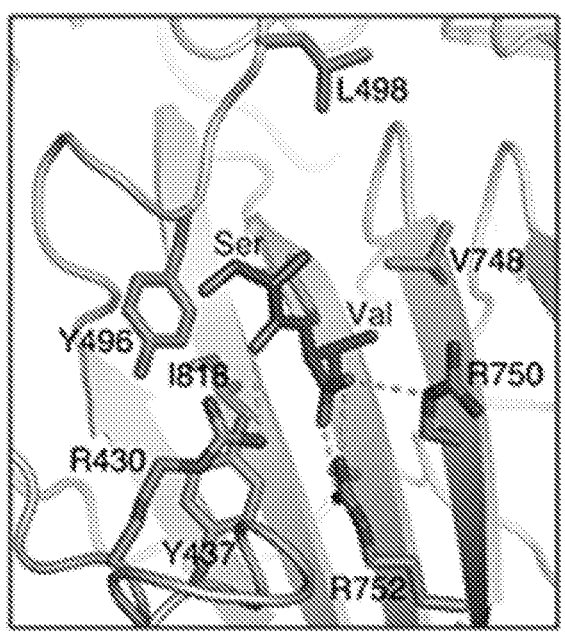

FIG. 7(E) demonstrates the binding mode of the DxE motif of vesicular stomatitis virus G protein complexed with Sec24a FIG. 7(F) shows a bound ΦC sequence containing a terminal Ser-Val motif.

Figure 8:
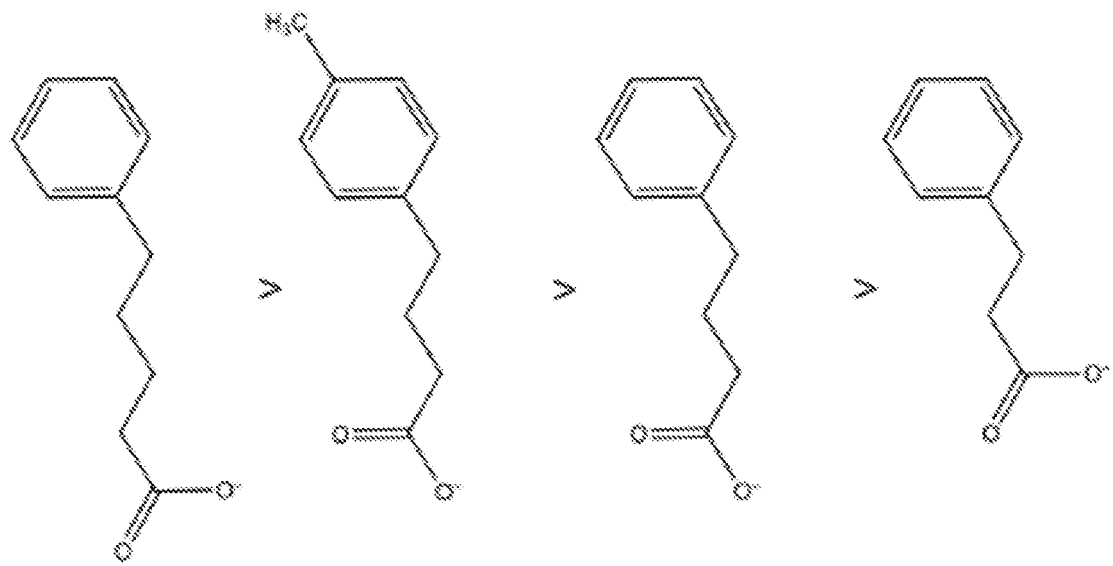
Figure 8:
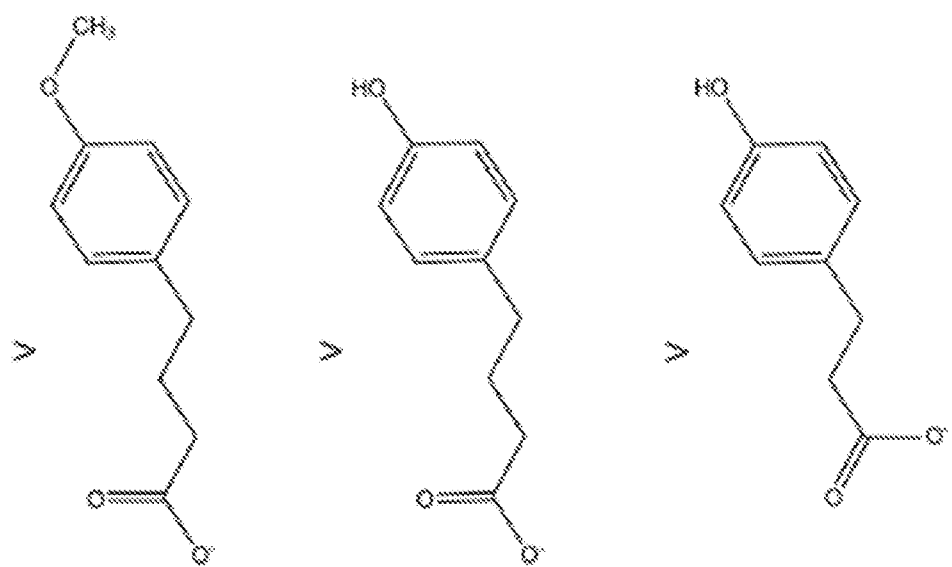

FIG. 8 shows the structural formulae for 4-PBA analogs in order of their affinity for COPII protein.

DETAILED DESCRIPTION

Recent advances in checkpoint inhibitor immunotherapy have highlighted the central importance of tumor neoantigens in the recognition of cancer cells by the immune system (R. D. Schreiber & T. N. Schumacher, Science 348, 69-74 (2015)). GRP94 (a.k.a. gp96) purified from tumor tissue is associated with tumor neoantigens, and is highly immunogenic via both the adaptive and innate immune pathways (Binder et al., *J Immunol* 179: 7254-7261 (2007); Strbo et al., *Vaccine* 29, 2619-2625 (2011)). The gp96/GRP94 protein is localized in the endoplasmic reticulum (ER) of cells, where it interacts with the ER reservoir of antigenic peptides (e.g., viral antigens, tumor neoantigens) being loaded onto MHC class I molecules. However, gp96:neoantigen complexes are stringently retained intracellularly by a mechanism of ER retention. Specifically, GRP94 maintains its residence in the ER via a combination of KDEL-mediated retrieval (i.e., the C-terminal KDEL sequence (SEQ ID NO: 3) in GRP94 serves as an ER retrieval signal for the KDEL receptor (see Munro & Pelham Cell 48:899-907 (1987)) and COPII-mediated retention (See Example 6 described herein).

The present disclosure provides compositions and methods for stimulating the extracellular secretion of large quantities of gp96/GRP94:antigen complexes, which is useful in eliciting an immune response via the adaptive and innate immune pathways. Further, the methods of the present technology may be used in combination with checkpoint blockade inhibitors to treat cancer.

It is to be appreciated that certain aspects, modes, embodiments, variations and features of the present technology are described below in various levels of detail in order to provide a substantial understanding of the present technology. The definitions of certain terms as used in this specification are provided below. Unless defined otherwise, all technical and scientific terms used herein generally have the same meaning as commonly understood by one of ordinary skill in the art to which this present technology belongs.

As used in this specification and the appended claims, the singular forms "a", "an" and "the" include plural referents unless the content clearly dictates otherwise. For example, reference to "a cell" includes a combination of two or more cells, and the like.

As used herein, the "administration" of a composition to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

As used herein, an "adjuvant" refers to one or more substances that stimulate or enhance the immune system of the subject. Adjuvants can include, for example, oil-in-water emulsions, water-in oil emulsions, alum (aluminum salts), liposomes and microparticles, such as, polysytrene, starch, polyphosphazene and polylactide/polyglycosides. Examples of adjuvants include, but are not limited to, squalene mixtures (SAF-I), muramyl peptide, saponin derivatives, *mycobacterium* cell wall preparations, monophosphoryl lipid A, mycolic acid derivatives, nonionic block copolymer surfactants, Quil A, cholera toxin B subunit, polyphosphazene and derivatives, and immunostimulating complexes (ISCOMs) such as those described by Takahashi et al., *Nature* 344: 873-875 (1990). Various appropriate adjuvants are known in the art (see, for example, Warren and Chedid, *CRC Critical Reviews in Immunology* 8: 83(1988); Allison and Byars, in Vaccines: New Approaches to Immunological Problems, Ellis, ed., Butterworth-Heinemann, Boston (1992)). Additional adjuvants include, for example, Freund's adjuvant (both complete and incomplete), bacille Calmett-Guerin (BCG), DETOX (containing cell wall skeleton of *Mycobacterium phlei* (CWS) and monophosphoryl lipid A from *Salmonella minnesota* (MPL)), and the like (see, for example, Hoover et al., *J. Clin. Oncol.*, 11: 390 (1993); Woodlock et al., *J. Immunotherapy* 22: 251-259 (1999)).

As used herein, an "antigen" refers to a molecule to which an antibody (or antigen binding fragment thereof) can selectively bind. The target antigen may be a protein, carbohydrate, nucleic acid, lipid, hapten, or other naturally occurring or synthetic compound. Exposure to an antigen may elicit an immune response in the subject.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease or condition, a positive control (a compound or composition known to exhibit the desired therapeutic effect) and a negative control (a subject or a sample that does not receive the therapy or receives a placebo) are typically employed.

As used herein, the term "effective amount" refers to a quantity sufficient to achieve a desired effect, e.g., an amount which results in increased extra cellular levels of GRP94 or increased secretion of GRP94 from cells. The compositions can also be administered in combination with one or more additional compounds or agents.

As used herein, "immune response" refers to the action of one or more of lymphocytes, antigen presenting cells, phagocytic cells, granulocytes, and soluble macromolecules produced by the aforementioned cells or the liver or spleen (including antibodies, cytokines, and complement) that results in selective damage to, destruction of, or elimination from the human body of cancerous cells, metastatic tumor cells, infectious pathogens etc. An immune response may include a cellular response, such as a T-cell response, or a humoral (antibody) response.

As used herein, the terms "individual", "patient", or "subject" can be an individual organism, a vertebrate, a mammal, or a human. In some embodiments, the individual, patient or subject is a human.

As used herein, the term "neoantigen" refers to a class of tumor antigens that arises from one or more tumor-specific mutations. Tumor neoantigens, which arise as a result of genetic change (e.g., inversions, translocations, deletions, missense mutations, splice site mutations, etc.) within malignant cells, represent the most tumor-specific class of antigens.

As used herein, the terms "polypeptide", "peptide" and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art. Such modifications are well described in basic texts and in more detailed monographs, as well as in a voluminous research literature.

As used herein, the term "simultaneous administration" refers to the administration of at least two active ingredients by the same route and at the same time or at substantially the same time.

As used herein, the term "separate administration" refers to the administration of at least two active ingredients at the same time or at substantially the same time by different routes.

As used herein, the term "sequential administration" refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, a "synergistic effect" refers to a greater-than-additive effect which is produced by a combination of at least two therapeutic agents, e.g., 4-PBA and one or more checkpoint inhibitors or immune system stimulators, and which exceeds that which would otherwise result from administration of any individual therapeutic agent alone. For example, lower doses of one or more therapeutic agents may be used in treating cancer, resulting in increased therapeutic efficacy and decreased side-effects.

"Treating", "treat", or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments, treatment means that the symptoms associated with the disease are, e.g., alleviated, reduced, cured, or placed in a state of remission.

It is also to be appreciated that the various modes of treatment or prevention of medical diseases and conditions as described are intended to mean "substantial," which includes total but also less than total treatment or prevention, and wherein some biologically or medically relevant result is achieved. The treatment may be a continuous prolonged treatment for a chronic disease or a single, or few time administrations for the treatment of an acute condition.

ER Trafficking

The secretory pathway in eukaryotic cells is responsible for biogenesis and proper intracellular distribution of a wide range of proteins, complex carbohydrates and lipids. Trafficking in the secretory pathway is highly dynamic and responsive to specific cellular functional demands. Forward transport (also known as anterograde transport) of newly synthesized proteins and lipids is initiated at the endoplasmic reticulum (ER) and, as such, ER-to-Golgi transport represents a vital gateway to the endomembrane system.

Membrane traffic between the ER and the Golgi is bidirectional and occurs via similar mechanisms. In both cases, a carrier forms on the donor organelle and then tethers to and fuses with the target organelle. Distinct machineries facilitate the formation of carriers for anterograde and retrograde transport, which are thought to ensure fidelity and directionality of trafficking: coat protein complex II (COPII) operates in the anterograde pathway from the ER, and coat protein complex I (COPI) functions in the retrograde route from the Golgi.

The COPII machinery includes the secretion-associated RAS-related 1 GTPase (SAR1) and the two sub-complexes SEC23-SEC24 and SEC13-SEC31. Activation of SAR1 is coordinated by the ER membrane-anchored guanine nucleotide exchange factor (GEF) SEC12, which produces the GTP-bound form of SAR1. Active SAR1 binds the ER membrane through an amino-terminal α-helix. SAR1 recruits SEC23-SEC24 heterodimers through interaction with the SEC23 subunit, which functions as a GTPase-activating protein (GAP) for SAR1. Although diffusion or 'bulk-flow' of cargo into COPII carriers occurs, it has been shown that COPII subunits can recognize specific ER export signals on membrane proteins for selective uptake.

The present technology relates to methods and compositions for modifying the trafficking of peptides and/or proteins from the ER.

4-phenylbutyrate and Analogues

In one aspect, the compositions useful in the methods disclosed herein are 4-phenylbutyrate (4-PBA), a compound of Formula I, and/or a 4-PBA analog where the 4-PBA analog is selected from 4-(4-methoxyphenyl)butyrate (methoxy-PBA), 3-phenylpropionate (3-PPA), 5-phenyl-valerate (5-PVA), 3-(4-hydroxyphenyl)propionate (hydroxy-PPA), 4-(4-hydroxyphenyl)butyrate (hydroxy-PBA), and 4-(4-tolyl)butyrate (tolyl-BA). See FIG. 8.

In some embodiments, 4-PBA and 4-PBA analogs are compounds of Formula I:

(Formula I)

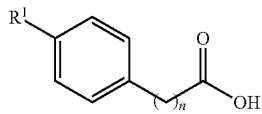

(I)

or a pharmaceutically acceptable salt thereof; wherein $R^1$ is H, $C_1$-$C_3$ alkyl, $C_1$-$C_3$ alkoxy, hydroxyl, thiol, $C_1$-$C_3$ alkylthio, —S(O)$R^2$, —S(O)$_2R^3$, or —S(O)$_2OR^4$; $R^2$, $R^3$, and $R^4$ are independently $C_1$-$C_3$ alkyl; and n is 2, 3, or 4.

Generally, reference to a certain element such as hydrogen or H is meant to include all isotopes of that element. For example, if an R group is defined to include hydrogen or H, it also includes deuterium and tritium. Compounds comprising radioisotopes such as tritium, $^{14}C$, $^{32}P$, and $^{35}S$ are thus within the scope of the present technology. Procedures for inserting such labels into the compounds of the present technology will be readily apparent to those skilled in the art based on the disclosure herein.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2, 2-dimethylpropyl groups.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like.

The term "thiol" refers to —SH groups. An alkylthio group is a sulfide (e.g., $C_1$-$C_3$ alkyl-S—).

As used herein, $C_m$-$C_n$, such as $C_1$-$C_{12}$, $C_1$-$C_8$, or $C_1$-$C_6$ when used before a group refers to that group containing m to n carbon atoms. For example, $C_1$-$C_3$ refers to a group that contains 1, 2, or 3 carbon atoms.

Pharmaceutically acceptable salts of compounds described herein are within the scope of the present technology and include acid or base addition salts, which retain the desired pharmacological activity and are not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., $Na^+$, $K^+$, $Ca^{2+}$, $Mg^{2+}$, $Zn^{2+}$), ammonia or organic amines (e.g., dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

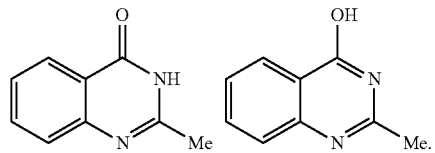

As another example, guanidines may exhibit the following isomeric forms in protic organic solution, also referred to as tautomers of each other:

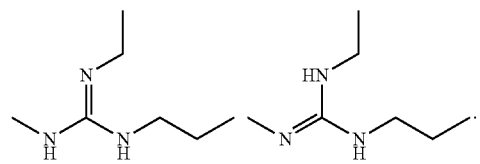

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

Methods for Modifying the Trafficking of Peptides and Proteins from the Endoplasmic Reticulum The present disclosure provides method for modifying the trafficking of peptides and/or proteins from the ER comprising contacting one or more cells with an effective amount of 4-phenylbutyrate (4-PBA), a compound of Formula I, and/or a 4-PBA analog selected from 4-(4-methoxyphenyl)butyrate (methoxy-PBA), 3-phenylpropionate (3-PPA), 5-phenylvalerate (5-PVA), 3-(4-hydroxyphenyl)propionate (hydroxy-PPA), 4-(4-hydroxyphenyl)butyrate (hydroxy-PBA), and 4-(4-tolyl)butyrate (tolyl-BA). In another embodiment, the method modifying the trafficking of peptides and/or proteins from the ER includes administering an effective amount of 4-PBA, a compound of Formula I, and/or a 4-PBA analog selected from among methoxy-PBA, 3-PPA, 5-PVA, hydroxy-PPA, hydroxy-PBA, and tolyl-BA, to a subject in need thereof.

In some embodiments, contacting a cell with an effective amount of 4-PBA, a compound of Formula I, and/or a 4-PBA analog selected from among methoxy-PBA, 3-PPA, 5-PVA, hydroxy-PPA, hydroxy-PBA, and tolyl-BA, promotes COPII packaging of ER resident and/or ER-trapped misfolded or unfolded proteins. In certain embodiments, contacting a cell with an effective amount of 4-PBA, a compound of Formula I, and/or a 4-PBA analog selected from among methoxy-PBA, 3-PPA, 5-PVA, hydroxy-PPA, hydroxy-PBA, and tolyl-BA, increases trafficking and/or secretion of ER resident and/or ER-trapped misfolded or unfolded proteins out of the ER.

Additionally or alternatively, in some embodiments, 4-PBA, a compound of Formula I, methoxy-PBA, 3-PPA, 5-PVA, hydroxy-PPA, hydroxy-PBA, or tolyl-BA binds to COPII. In certain embodiments, 4-PBA, a compound of Formula I, methoxy-PBA, 3-PPA, 5-PVA, hydroxy-PPA, hydroxy-PBA, or tolyl-BA binds to Sec24a of COP II. In some embodiments, 4-PBA, a compound of Formula I, methoxy-PBA, 3-PPA, 5-PVA, hydroxy-PPA, hydroxy-PBA, or tolyl-BA binds to the B site of Sec24a.

Additionally or alternatively, in some embodiments, contacting one or more cells with an effective amount of 4-PBA, a compound of Formula I, methoxy-PBA, 3-PPA, 5-PVA, hydroxy-PPA, hydroxy-PBA, and/or tolyl-BA reduces ER packaging of p24 proteins and/or ERGIC-53 proteins. By way of example, but not by way of limitation, in some embodiments, the p24 proteins are p24δ1, p24α2, p24α3 and p24β1.

Modifying the Trafficking of GRP94, GRP170, and Calreticulin

The present technology provides methods and compositions for increasing the extra cellular levels of GRP94, GRP170, and calreticulin, comprising contacting one or more cells with an effective amount of 4-phenylbutyrate (4-PBA), a compound of Formula I, and/or a 4-PBA analog selected from Formula I, 4-(4-methoxyphenyl)butyrate (methoxy-PBA), 3-phenylpropionate (3-PPA), 5-phenylvalerate (5-PVA), 3-(4-hydroxyphenyl)propionate (hydroxy-PPA), 4-(4-hydroxyphenyl)butyrate (hydroxy-PBA), and 4-(4-tolyl)butyrate (tolyl-BA).

In some embodiments, the one or more cells are cells under ER stress. ER stress is a perturbance in ER function that disrupts protein folding in the ER. By way of example, but not by way of limitation, causes of ER stress include hypoxia, nutrient (e.g., glucose) deprivation, alterations in the redox balance, changes in calcium homeostasis, failure of posttranslational modifications, and increases in general protein synthesis. ER stress can lead to the accumulation of unfolded and misfolded proteins in the ER. Eukaryotic cells have developed an evolutionarily conserved adaptive mechanism, the unfolded protein response (UPR), which functions to clear unfolded proteins and restore ER homeostasis.

ER stress can be measured by using methods commonly known in the art. For example, ER stress can be measured by ER dilation, real-time redox measurements during ER stress, and measuring the activation of UPR (e.g., measuring IRE1α, PERK, or ATE6α activation).

In some embodiments, the one or more cells are cancer cells. By way of example, but not by way of limitation, in some embodiments, the cancer cell is selected from liver cancer cells, myeloma cells, colorectal cancer cells, lung cancer cells, pancreatic cancer cells, breast cancer cells, prostate cancer cells and the like. The one or more cells may be pre-cancerous cells or dysplastic cells.

In one aspect, the present disclosure provides a method for increasing extracellular secretion of GRP94 by one or more cells in a subject in need thereof comprising administering to the subject an effective amount of 4-PBA, a compound of Formula I, and/or a 4-PBA analog selected from among methoxy-PBA, 3-PPA, 5-PVA, hydroxy-PPA, hydroxy-PBA, and tolyl-BA. 4-PBA, the compound of Formula I, and/or the 4-PBA analog may be administered orally, topically, intranasally, systemically, intravenously, subcutaneously, intraperitoneally, intradermally, intraocularly, iontophoretically, transmucosally, or intramuscularly. Additionally or alternatively, in some embodiments, the one or more cells are cells under ER stress.

In certain embodiments, the subject is diagnosed with or suffers from cancer. Examples of cancer include bladder cancer, breast cancer, cervical cancer, colon cancer, esophageal cancer, endometrial cancer, gastric cancer, glioblastoma, head and neck cancer, hepatocellular carcinoma, leukemia, lung cancer, lymphoma, melanoma, Merkel cell carcinoma, multiple myeloma, neuroblastoma, neuroendocrine cancer, non-small cell lung cancer, ovarian cancer, pancreatic cancer, prostate cancer, rectal cancer, renal cell carcinoma, rhabdoid cancer, sarcoma, or urinary tract cancer. Additionally or alternatively, in some embodiments, the secreted GRP94 is complexed with tumor neoantigens.

Additionally or alternatively, in some embodiments, the subject is infected with a virus. The virus may be selected from the group consisting of human immunodeficiency virus (HIV), herpes simplex virus (HSV), influenza virus, EBV, Ebola virus, chicken pox virus, Hepatitis B virus, Hepatitis C virus, HPV, rubeola virus, rubulavirus, rubella virus, poliovirus, Rous Sarcoma Virus, rabies virus, and rotavirus. Additionally or alternatively, in some embodiments, the secreted GRP94 is complexed with viral antigens.

In some embodiments of the methods disclosed herein, an increase in extra cellular levels or increased secretion of GRP94, GRP170, and/or calreticulin elicits or induces an immune response. In some embodiments, the immune response is an anti-tumor immune response.

Saturation of ER Retrieval Systems

The present technology provides methods and compositions for saturating one or more ER retrieval systems in one or more cells, the method including contacting the one or more cells with an effective amount of 4-phenylbutyrate (4-PBA), a compound of Formula I, and/or a 4-PBA analog selected from 4-(4-methoxyphenyl)butyrate (methoxy-PBA), 3-phenylpropionate (3-PPA), 5-phenylvalerate (5-PVA), 3-(4-hydroxyphenyl)propionate (hydroxy-PPA), 4-(4-hydroxyphenyl)butyrate (hydroxy-PBA), and 4-(4-tolyl)butyrate (tolyl-BA). In some embodiments, the one or more cells are cells under ER stress and/or are cancer cells.

Additionally or alternatively, in some embodiments, the one or more ER retrieval systems are selected from the group consisting of the KDEL-mediated retrieval system, the Rer1 retrieval system, dilysine (KKxx) retrieval system, and the Erv41-Erv46 retrieval system.

Therapeutic Methods of the Present Technology

In one aspect, the present disclosure provides a method for treating cancer in a subject in need thereof comprising administering to the subject an effective amount of 4-PBA, a compound of Formula I, and/or a 4-PBA analog selected from among methoxy-PBA, 3-PPA, 5-PVA, hydroxy-PPA, hydroxy-PBA, and tolyl-BA. 4-PBA, the compound of Formula I, and/or the 4-PBA analog is administered orally, topically, intranasally, systemically, intravenously, subcutaneously, intraperitoneally, intradermally, intraocularly, iontophoretically, transmucosally, or intramuscularly. In some embodiments, one or more cells of the subject are under endoplasmic reticulum (ER) stress. In certain embodiments, the one or more cells under ER stress are cancer cells. Additionally or alternatively, in some embodiments, the subject is human. In some embodiments, 4-PBA, the compound of Formula I, and/or the 4-PBA analog binds to COPII protein.

In any of the above embodiments of the methods disclosed herein, the cancer is bladder cancer, breast cancer, cervical cancer, colon cancer, esophageal cancer, endometrial cancer, gastric cancer, glioblastoma, head and neck cancer, hepatocellular carcinoma, leukemia, lung cancer, lymphoma, melanoma, Merkel cell carcinoma, multiple myeloma, neuroblastoma, neuroendocrine cancer, non-small cell lung cancer, ovarian cancer, pancreatic cancer, prostate cancer, rectal cancer, renal cell carcinoma, rhabdoid cancer, sarcoma, or urinary tract cancer.

Additionally or alternatively, in some embodiments, administration of 4-PBA, the compound of Formula I, and/or the 4-PBA analog results in increased GRP94 extracellular levels in the subject (e.g., at least 1.5 fold, at least 2 fold, at least 2.5 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, or at least 10 fold) compared to that observed in the subject prior to administration.

Additionally or alternatively, in some embodiments, 4-PBA, the compound of Formula I, and/or the 4-PBA analog is administered daily for 6 weeks or more. In some embodiments, 4-PBA, the compound of Formula I, and/or the 4-PBA analog is administered daily for 12 weeks or more.

In one aspect, the present disclosure provides a method for enhancing cancer immunotherapy in a subject in need thereof comprising administering to the subject an effective amount of 4-PBA, a compound of Formula I, and/or a 4-PBA analog selected from among methoxy-PBA, 3-PPA, 5-PVA, hydroxy-PPA, hydroxy-PBA, and tolyl-BA. In some embodiments, administration of 4-PBA, the compound of Formula I, and/or the 4-PBA analog results in elevated secretion of GRP94/neoantigen complexes in the subject compared to that observed in the subject prior to administration. In some embodiments, the GRP94/neoantigen complexes may comprise neoantigenic peptides that are about 5 to about 50 amino acids in length.

In certain embodiments, the GRP94/neoantigen complexes may comprise neoantigenic peptides that are about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 60, about 70, about 80, about 90, about 100, about 110, or about 120 amino acids in length, or any range derivable therein. Additionally or alternatively, in some embodiments, the neoantigenic peptides comprise a tumor specific mutation (e.g., a driver mutation for a particular cancer type).

Additionally or alternatively, in some embodiments, the subject is diagnosed with a cancer selected from the group consisting of bladder cancer, breast cancer, cervical cancer, colon cancer, esophageal cancer, endometrial cancer, gastric cancer, glioblastoma, head and neck cancer, hepatocellular carcinoma, leukemia, lung cancer, lymphoma, melanoma, Merkel cell carcinoma, multiple myeloma, neuroblastoma, neuroendocrine cancer, non-small cell lung cancer, ovarian cancer, pancreatic cancer, prostate cancer, rectal cancer, renal cell carcinoma, rhabdoid cancer, sarcoma, and urinary tract cancer.

In some embodiments, the enhancement of cancer immunotherapy is characterized by a greater reduction in tumor size in a subject undergoing cancer immunotherapy and administered a compound of the present technology (4-PBA, the compound of Formula I, and/or the 4-PBA analog) as compared to a subject undergoing cancer immunotherapy alone.

In another aspect, the present disclosure provides a method for enhancing viral immunotherapy in a subject in need thereof comprising administering to the subject an effective amount of 4-PBA, a compound of Formula I, and/or a 4-PBA analog selected from among methoxy-PBA, 3-PPA, 5-PVA, hydroxy-PPA, hydroxy-PBA, and tolyl-BA. In some embodiments, administration of 4-PBA, the compound of Formula I, and/or the 4-PBA analog results in elevated secretion of GRP94/viral antigen complexes in the subject compared to that observed in the subject prior to administration. Additionally or alternatively, in some embodiments, the subject is infected with a virus selected from the group consisting of human immunodeficiency virus (HIV), herpes simplex virus (HSV), influenza virus, EBV, Ebola virus, chicken pox virus, Hepatitis B virus, Hepatitis C virus, HPV, rubeola virus, rubulavirus, rubella virus, poliovirus, Rous Sarcoma Virus, rabies virus, and rotavirus.

In some embodiments of the methods disclosed herein, the enhancement of viral immunotherapy is characterized by an increase in antibody production to an antigen in a subject undergoing viral immunotherapy and administered a compound of the present technology (4-PBA, the compound of Formula I, and/or the 4-PBA analog) as compared to a subject undergoing viral immunotherapy alone.

Additionally or alternatively, in some embodiments of the methods disclosed herein, 4-PBA, the compound of Formula I, and/or the 4-PBA analog is administered orally, topically, intranasally, systemically, intravenously, subcutaneously, intraperitoneally, intradermally, intraocularly, iontophoretically, transmucosally, or intramuscularly.

In any of the foregoing embodiments, the methods of the present technology further comprise administering an effective amount of an adjuvant to the subject. Additionally or alternatively, in some embodiments, the methods further comprise separately, sequentially or simultaneously administering one or more checkpoint inhibitors disclosed herein and/or one or more immune system stimulators disclosed herein.

In another aspect, the present technology relates to methods of treating pre-cancerous cells or dysplastic cells, wherein the method includes administration of an effective amount of 4-phenylbutyrate (4-PBA), a compound of Formula I, and/or a 4-PBA analog, selected from 4-(4-methoxyphenyl)butyrate (methoxy-PBA), 3-phenylpropionate (3-PPA), 5-phenylvalerate (5-PVA), 3-(4-hydroxyphenyl) propionate (hydroxy-PPA), 4-(4-hydroxyphenyl)butyrate (hydroxy-PBA), and 4-(4-tolyl)butyrate (tolyl-BA) to a subject in need thereof. In some embodiments, the treatment of pre-cancerous cells or dysplastic cells is characterized by the reduction of pre-cancerous cells or dysplastic cells.

Modes of Administration and Effective Amounts

Any method known to those in the art for contacting a cell, organ, or tissue with 4-PBA, a compound of Formula I, and/or a 4-PBA analog selected from among methoxy-PBA, 3-PPA, 5-PVA, Hydroxy-PPA, Hydroxy-PBA, and tolyl-BA, may be employed. Suitable methods include in vitro, ex vivo, or in vivo methods. In vitro methods typically include the administration or contacting of 4-PBA, a compound of Formula I, and/or a 4-PBA analog selected from among methoxy-PBA, 3-PPA, 5-PVA, Hydroxy-PPA, Hydroxy-PBA, and tolyl-BA, to one or more cells. In some embodiments, the cell is a cancer cell. By way of example, but not by way of limitation, in some embodiments, the cancer cell is selected from among liver cancer cells, myeloma cells, colorectal cancer cells, lung cancer cells, pancreatic cancer cells, breast cancer cells, and prostate cancer cells.

In vivo methods of contacting cells typically include the administration of 4-PBA, a compound of Formula I, and/or a 4-PBA analog selected from among methoxy-PBA, 3-PPA, 5-PVA, hydroxy-PPA, hydroxy-PBA, and tolyl-BA, to a subject. In some embodiments, the subject is a mammal, e.g., a human. When used in vivo, 4-PBA, a compound of Formula I, methoxy-PBA, 3-PPA, 5-PVA, hydroxy-PPA, hydroxy-PBA, and tolyl-BA salt, are administered to the subject in effective amounts (i.e., amounts that have a desired effect, e.g., increased secretion of GRP94 from one or more cells). The effective amount will depend upon the characteristics of the 4-PBA, methoxy-PBA, 3-PPA, 5-PVA, hydroxy-PPA, hydroxy-PBA, and/or tolyl-BA used.

An effective amount of 4-PBA, a compound of Formula I, and/or 4-PBA analog selected from among methoxy-PBA, 3-PPA, 5-PVA, hydroxy-PPA, hydroxy-PBA, and tolyl-BA useful in the above methods may be administered to a subject in need thereof by any of a number of well-known methods for administering pharmaceutical compounds. 4-PBA, a compound of Formula I, and/or 4-PBA analog selected from among methoxy-PBA, 3-PPA, 5-PVA, hydroxy-PPA, hydroxy-PBA, and tolyl-BA are administered systemically or locally.

The compounds described herein, such as 4-PBA, can be incorporated into pharmaceutical compositions for administration, singly or in combination, to a subject. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

In some embodiments, the pharmaceutical compositions of the present technology are formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Systemic administration of the compound as described herein (e.g., 4-PBA) can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed by iontophoresis.

Dosage, toxicity and efficacy of 4-PBA, a compound of Formula I, and a 4-PBA analog selected from among methoxy-PBA, 3-PPA, 5-PVA, hydroxy-PPA, hydroxy-PBA, and tolyl-BA, can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are advantageous. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may be within a range of circulating concentrations that include the ED50 with little or no toxicity. The dosage may vary within this range depending upon the dosage form employed and the route of administration utilized. For any compound used in the methods, the effective amount can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to determine useful doses in humans accurately.

Levels in plasma may be measured, for example, by high performance liquid chromatography.

In some embodiments, an effective amount of 4-PBA, compound of Formula I, or a 4-PBA analog selected from among methoxy-PBA, 3-PPA, 5-PVA, hydroxy-PPA, hydroxy-PBA, and tolyl-BA, sufficient for achieving a desired effect, range from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of 4-PBA, the compound of Formula I, or the 4-PBA analog ranges from 0.001-10,000 micrograms per kg body weight. In one embodiment, an exemplary treatment regime entails administration once per day or once a week.

In some embodiments, an effective amount of 4-PBA, a compound of Formula I, or a 4-PBA analog selected from among methoxy-PBA, 3-PPA, 5-PVA, hydroxy-PPA, hydroxy-PBA, and tolyl-BA, is defined as a concentration of compound at the target tissue of $10^{-12}$ to $10^{-6}$ molar, e.g., approximately $10^{-7}$ molar. This concentration may be delivered by systemic doses of 0.001 to 100 mg/kg or equivalent dose by body surface area. The schedule of doses would be optimized to maintain the compound concentration at the target tissue, such as by single daily or weekly administration, but also including continuous administration (e.g., parenteral infusion or transdermal application).

In some embodiments, an effective amount of 4-PBA, a compound of Formula I, or a 4-PBA analog selected from among methoxy-PBA, 3-PPA, 5-PVA, hydroxy-PPA, hydroxy-PBA, and tolyl-BA is defined as between about 1 to 100 µM, 5 to 90 µM, 10 to 80 µM, 20 to 70 µM, 30 to 60 µM, or 40 to 50 µM.

In some embodiments, an effective amount of 4-PBA, a compound of Formula I, or a 4-PBA analog selected from among methoxy-PBA, 3-PPA, 5-PVA, hydroxy-PPA, hydroxy-PBA, and tolyl-BA is defined as between about 100 to 1000 µM, 200 to 900 µM, 300 to 800 µM, 400 to 700 µM, or 500 to 600 µIVI. In some embodiments, an effective amount of 4-PBA, a compound of Formula I, or a 4-PBA analog selected from among methoxy-PBA, 3-PPA, 5-PVA, hydroxy-PPA, hydroxy-PBA, and tolyl-BA is defined as about 700 µM, 800 µM, 900 µM, or 1000 µM, and any concentration between any two of the preceding concentrations.

In some embodiments, an effective amount of 4-PBA, a compound of Formula I, or a 4-PBA analog selected from among methoxy-PBA, 3-PPA, 5-PVA, hydroxy-PPA, hydroxy-PBA, and tolyl-BA is defined as between about 1000 to 1800 µM, 1100 to 1700 µM, 1200 to 1600 µM, or 1300 to 1500 µM.

In some embodiments, an effective amount of 4-PBA, a compound of Formula I, or a 4-PBA analog, selected from among methoxy-PBA, 3-PPA, 5-PVA, hydroxy-PPA, hydroxy-PBA, and tolyl-BA is defined as between about 1 to 40 mM, 5 to 35 mM, 10 to 30 mM, or 15 to 25 mM. In some embodiments, an effective amount of 4-PBA, a compound of Formula I, or a 4-PBA analog, selected from among methoxy-PBA, 3-PPA, 5-PVA, hydroxy-PPA, hydroxy-PBA, and tolyl-BA is defined as about 1, 5, 10, 15, 20, 25, 30, 35, or 40 mM, and any concentration between any two of the preceding concentrations.

In some embodiments, the above concentrations are the concentration of 4-PBA, a compound of Formula I, or a 4-PBA analog, selected from among methoxy-PBA, 3-PPA, 5-PVA, hydroxy-PPA, hydroxy-PBA, and tolyl-BA at the target tissue.

The skilled artisan will appreciate that certain factors may influence the dosage or concentration and timing required to elicit a desired response, e.g., increased secretion of GRP94. Moreover, administration to a subject or contacting cells with an effective amount of the compounds described herein can include a single treatment or a series of treatments.

The mammal administered a composition describe herein (e.g., 4-PBA) in accordance with the present methods can be any mammal, including, for example, farm animals, such as sheep, pigs, cows, and horses; pet animals, such as dogs and cats; laboratory animals, such as rats, mice and rabbits. In some embodiments, the mammal is a human.

For therapeutic applications, a composition of the present technology comprising 4-PBA, a compound of Formula I, and/or a 4-PBA analog selected from among methoxy-PBA, 3-PPA, 5-PVA, Hydroxy-PPA, Hydroxy-PBA, and tolyl-BA is administered to the subject. In some embodiments, the composition of the present technology is administered one, two, three, four, or five times per day. In some embodiments, the composition of the present technology is administered more than five times per day. Additionally or alternatively, in some embodiments, the composition of the present technology is administered every day, every other day, every third day, every fourth day, every fifth day, or every sixth day. In some embodiments, the composition of the present technology is administered weekly, bi-weekly, tri-weekly, or monthly. In some embodiments, the composition of the present technology is administered for a period of one, two, three, four, or five weeks. In some embodiments, the composition of the present technology is administered for six weeks or more. In some embodiments, the composition of the present technology is administered for twelve weeks or more. In some embodiments, the composition of the present technology is administered for a period of less than one year. In some embodiments, the composition of the present technology is administered for a period of more than one year. Additionally or alternatively, in some embodiments, the composition of the present technology is administered daily for one, two, three, four or five weeks. In some embodiments, the composition of the present technology is administered daily for less than 6 weeks. In some embodiments, the composition of the present technology is administered daily for 6 weeks or more. In other embodiments, the composition of the present technology is administered daily for 12 weeks or more.

Combination Therapy with Other Active Agents

In some embodiments, 4-PBA, a compound of Formula I, and/or a 4-PBA analog selected from among methoxy-PBA, 3-PPA, 5-PVA, hydroxy-PPA, hydroxy-PBA, and tolyl-BA, is combined or separately, sequentially or simultaneously administered with one or more checkpoint inhibitors and/or one or more immune system stimulators. The one or more checkpoint inhibitors may target PD-1, PD-L1 or CTLA-4.

In some embodiments, the one or more checkpoint inhibitors are selected from the group consisting of ipilimumab (Yervoy®; Bristol-Myers Squibb, Princeton, N.J.), pembrolizumab (Keytruda®; Merck, Whitehouse Station, N.J.), nivolumab (Opdivo®; Bristol-Myers Squibb, Princeton, N.J.), atezolizumab (Tecentriq®; Genetech, San Francisco, Calif.), avelumab (Bavencio®; Merck, Whitehouse Station, N J and Pfizer, New York, N.Y.), and durvalumab (Imfinzi®; AstraZeneca, Cambridge, UK), pidilizumab (Curetech Ltd., Yavne, Israel), AMP-224 (GlaxoSmithKline, La Jolla, Calif.), MPDL3280A (Roche, Basel, Switzerland), MDX-1105 (Bristol Myer Squibb, Princeton, N.J.), MEDI-4736 (Medimmune, Gaithersburg, Md.), arelumab (Merck Serono, Darmstadt, Germany), tremelimumab (Pfizer, New York, N.Y.), IMP321 (Immutep S.A., New South Wales, Australia), MGA271 (Macrogenics, Rockville, Md.), BMS-986016 (Bristol-Meyers Squibb, Princeton, N.J.), lirilumab (Bristol-Myers Squibb, Princeton, N.J.), urelumab (Bristol-Meyers Squibb, Princeton, N.J.), PF-05082566 (Pfizer, New York, N.Y.), IPH2101 (Bristol-Myers Squibb, Princeton, N.J.), MEDI-6469 (MedImmune, Gaithersburg, Md.), CP-870,893 (Genentech, Oceanside, Calif.), Mogamulizumab (Kyowa Hakko Kirin, La Jolla, Calif.), Varlilumab (CellDex Therapeutics, Hampton, N.J.), Galiximab (Biogen Idec, Cambridge, Mass.), AMP-514 (Amplimmune, Gaithersburg, Md.), AUNP 12 (Aurigene, Bangalore, India), Indoximod (NewLink Genetics, Ames, Iowa), NLG-919 (NewLink Genetics, Ames, Iowa), INCB024360 (Incyte, Wilmington, Del.) and any combination thereof.

By way of example, but not by way of limitation, in some embodiments, the one or more immune system stimulators are selected from among a natural killer cell (NK) stimulator, an antigen presenting cell (APC) stimulator, a granulocyte macrophage colony-stimulating factor (GM-CSF), and a toll-like receptor stimulator.

In some embodiments, the NK stimulator includes, but is not limited to, IL-2, IL-15, IL-15/IL-15RA complex, IL-18, and IL-12. In some embodiments, the NK stimulator includes an antibody that stimulates at least one of the following receptors NKG2, KIR2DL1/S1, KRI2DL5A, NKG2D, NKp46, NKp44, or NKp30.

In some embodiments, the APC stimulator includes, but is not limited to, CD28, inducible costimulatory (ICOS), CD40, CD30, CD27, OX-40, and 4-1BB.

In some embodiments, 4-PBA a compound of Formula I, and/or a 4-PBA analog selected from among methoxy-PBA, 3-PPA, 5-PVA, hydroxy-PPA, hydroxy-PBA, and tolyl-BA, and one or more checkpoint inhibitors and/or one or more immune system stimulators are administered in any order or even simultaneously. If simultaneously, the multiple therapeutic agents may be provided in a single, unified form, or in multiple forms (by way of example only, either as a single pill or as two separate pills). One of the above compounds may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents. In some embodiments, the combination of 4-PBA a compound of Formula I, and/or 4-PBA analog selected from among methoxy-PBA, 3-PPA, 5-PVA, hydroxy-PPA, hydroxy-PBA, and tolyl-BA and one or more checkpoint inhibitors and/or one or more immune system stimulators results in a synergistic effect.

EXAMPLES

The present technology is further illustrated by the following examples, which should not be construed as limiting in any way.

General Methods
Expression Vectors

In the present examples, constructs for *H. sapiens* Sec24a (Δ1-340), full-length Sec24d and full-length Sec31a that were cloned into the vector pFast-HTB (Invitrogen), encoding a tobacco etch virus (TEV) cleavable N-terminal His6 tag. Vectors encoding *H. sapiens* full-length Sec23a and Sec13a were of the type pFastBac1 (Invitrogen). The full-length Sec24d L750W mutant was generated using the Phusion site-directed mutagenesis kit (New England Biolabs). One pair of 5'-phosphorylated primers (forward, TGGTA CACGA CAATC AGTGG TCAA (SEQ ID NO: 5); reverse, CACAG CACAC TGGAT TAAGG CTCC (SEQ ID NO: 6)) was used to generate Sec24d L750W DNA from the wildtype Sec24d template. Recombinant bacmids were generated in DHIOBac cells transformed with the various pFastBac vectors, using the Bac-to-Bac baculovirus expression system (Invitrogen).

DNA for full-length *H. sapiens* Sar1a was cloned into the vector pGEX-6P-1 (GE Life Sciences), resulting in a protein with a N-terminal prescission protease (Invitrogen) cleavable glutathione S-transferase (GST) tag (protease cleavage yields the N-terminal sequence GPLGSMSFI (SEQ ID NO: 7)).

DNA encoding *H. sapiens* Sec22b (residues 1-195) was cloned in the PET-28b vector (Novagen) with an additional N-terminal His$_6$-Smt3 fusion ("His6" disclosed as SEQ ID NO: 4), as described in Mancias and Goldberg (2007).

DNA encoding full-length *H. sapiens* LDL receptor (wild type and G544V forms) was cloned into the tetracycline-inducible expression vector pcDNA4/TO (Invitrogen) as described (Sorensen et al. (2006) and Tveten et al. (2007)). The G544V mutant LDL receptor was generated with Phusion site-directed mutagenesis kit, using two 5'-phosphorylated primers as follows: forward, GTCATC ACCCT AGATC TCCTC AGT (SEQ ID NO: 8); reverse, ATTGG GCCAC TGAAT GTTTT CAGT (SEQ ID NO: 9). The correct construction of all recombinant plasmid was confirmed by DNA sequencing (Genewiz, Inc.).

Protein and Peptide Production

The expression in High Five insect cells (Invitrogen) and purification of COPII protein complexes were carried out essentially as described in Mancias and Goldberg (2008). This includes the complex of Sec23a/Sec24a(Δ1-340) used for X-ray crystallography, Sec23a/Sec24d (full-length protein) for COPII budding assays, and Sec24a(Δ1-340) for fluorescence polarization experiments.

In preparation for protein production, recombinant baculoviruses were generated by transfecting *Spodoptera frugiperda* (Sf9) cells with bacmid DNA using the Cellfectin II Reagent (Invitrogen). Baculoviruses were amplified for three generations then used to infect High Five insect cells. Cells were harvested 48 h post-infection and resuspended in a lysis buffer (50 mM Tris-HCl pH 8.0, 500 mM NaCl, 1 mM β-mercaptoethanol, 1 mM phenylmethylsulfonyl fluoride (PMSF) and protease inhibitor cocktail (Roche)).

Sec23a/Sec24a (Δ1-340) and Sec24a (Δ1-340) proteins were purified from cell lysates by HisTrap HP chromatography (GE Life Sciences) and the His6 tag (SEQ ID NO: 4) was removed using TEV protease (Invitrogen) at 4° C. during overnight dialysis against a solution comprising 50 mM Tris-HCl pH 8.0, 300 mM NaCl and 5 mM Dithiothreitol (DTT). COPII proteins were diluted 3-fold with a low-salt buffer (50 mM Tris-HCl pH 8.5, 50 mM NaCl and 5 mM DTT) and loaded into a 5 ml HiTrap Q column (GE Life Sciences) followed by gradient elution with 50 mM Tris-HCl pH 8.0, 250 mM NaCl and 5 mM DTT. Finally, the protein was purified by size exclusion chromatography on a HiLoad 26/60 Superdex 200 column (GE Life Sciences) in 20 mM Tris-HCl pH 7.5, 200 mM NaCl and 4 mM DTT.

The full-length Sec23a/Sec24d proteins, wild type and L750W mutant, and Sec13a/31a protein used in budding experiments were purified in the same manner, except that N-terminal His6 tags (SEQ ID NO: 4) were not removed. Following the affinity purification step, proteins were diluted directly (rather than dialyzed) into low salt buffer, followed by chromatographic purification using HiTrap Q followed by HiLoad 26/60 Superdex 200 columns in buffer 20 mM Tris-HCl pH 7.5, 500 mM NaCl and 1 mM DTT.

The full-length *H. sapiens* Sar1a protein was expressed in *E. coli* BL21(DE3) (Invitrogen) in Luria-Bertani (LB) broth. At a culture density of $OD_{600}$=0.8, protein expression was induced by the addition of 0.2 mM isopropyl β-D-1-thiogalactopyranoside at 16° C. overnight. GST-tagged Sar1a was purified first on a GST-Trap 4B column (GE Life Sciences) in PBS buffer (10 mM Na2HPO4 pH 7.4, 137 mM NaCl, 2.7 mM KCl, 1 mM PMSF). The GST tag was removed with precision protease and Sar1a was purified further by size exclusion Superdex 75 chromatography in a buffer containing 20 mM Tris-HCl pH 7.5, 500 mM NaCl and 1 mM DTT, as described in Kim et al. (2005)).

The cytosolic region (residues 1-195) of *H. sapiens* Sec22b was purified as described Mancias and Goldberg (2007). Briefly, the protein was expressed in *E. coli* with an N-terminal His6-Smt3 tag ("His6" disclosed as SEQ ID NO: 4). Following removal of the tag with Ulp1 protease, protein was purified on a Hi-Trap Q column, then by size exclusion Superdex 75 chromatography in 20 mM Tris-HCl pH 7.5, 200 mM NaCl and 4 mM DTT. All purified proteins were concentrated, aliquoted, flash frozen and stored at –80° C.

Synthetic peptides containing the ΦC signal motif, at >95% purity, were purchased from the Tufts University Core Facility (see Table 1 for full peptide sequences).

Protein Crystallization and Structure Determination

The Sec23a/Sec24a•Sec22b complex was crystallized as described in Mancias and Goldberg (2007) from a solution comprising 10% (w/v) PEG 4000, 500 mM Na acetate and 50 mM Tris-HCl pH 7.9. Crystals were transferred into a soaking buffer of 10% (w/v) PEG 4000, 600 mM NaCl, 50 mM Tris-HCl buffer, pH 7.9. Either 4-PBA (0-50 mM) or 5 mM ΦC signal peptide was added to the crystal containing solution, and the ligand soaking proceeded for five hours at 22° C. Crystals were then transferred to an equivalent ligand-containing buffer with additional 24% ethylene glycol cryo-protectant, and were flash frozen in liquid nitrogen. Crystals treated in this manner diffracted synchrotron X-rays to 2.5-2.8 Å resolution.

X-ray diffraction data were collected at 0.979 Å wavelength on beamline ID-24C or ID-24E of the Advanced Photon Source, Argonne National Laboratory. Data were processed with the program HKL2000 (Otwinowski and Minor (1997); see Tables 1 and 2). Structure refinement was carried out using Phenix (Adams et al. (2010)), initially by rigid-body improvement, followed by positional refinement, based on the published coordinates of Sec23a/Sec24a•Sec22b (PDB 2NUT; Mancias and Goldberg (2007)). Models for 1C signal peptides or 4-PBA were not included in refinements prior to the creation of FIG. 1, to eliminate potential phase bias. These ligands were modeled in a final stage of refinement, the statistics for which are summarized in Tables 1 and 2.

TABLE 1

Data Collection and Refinement Statistics - (ΦC signal complexes (Table 1 discloses SEQ ID NOS 1 and 10-15, respectively, in order of appearance)

| COPII pratein complex | Sec23/24 · 22 | Sec23/24 · 22 | Sec23/24 · 22 | Sec23/24 · 22 | Sec23/24 · 22 | Sec23/24 · 22 | Sec23/24 · 22 |
|---|---|---|---|---|---|---|---|
| Peptide | EVTSLV | EVTSVV | EVTSII | EVTSSV | EVTSFA | EVTSFF | EVTSLI |
| Protein Data Bank ID | | | | | | | |
| Space group: | C2 | C2 | C2 | C2 | C2 | C2 | C2 |
| Copies/asymmetric unit | 1 | 1 | 1 | 1 | 1 | 1 | 1 |
| Cell parameters a, b, c (Å) | 148.4, 96.8, 127.0 | 147.8, 97.1, 128.8 | 148.0, 96.9, 130.0 | 147.9, 96.9, 127.3 | 147.6, 96.1, 130.0 | 147.9, 96.9, 129.5 | 148.2, 97 130.5 |
| Cell parameters β (°) | 91.7 | 90.1 | 90.1 | 91.6 | 90.1 | 90.2 | 90.1 |
| Data processing | | | | | | | |
| Resolution (Å) | 50-2.7 | 50-2.6 | 50-2.6 | 50-2.6 | 50-2.8 | 50-2.8 | 50-2.6 |
| Rmerge (%)[a] | 8.9 (70.2) | 9.6 (52.0) | 11.4 (55.0) | 8.0 (77.4) | 11.6 (58.2) | 11.6 (58.2) | 12.6 (78.9) |
| I/σ | 24.5 (2.6) | 18.0 (1.5) | 16.2 (1.1) | 29.5 (2.5) | 12.6 (1.0) | 12.6 (1.0) | 30.1 (2.3) |
| Completeness (%) | 99.8 (100) | 99.0 (99.5) | 98.8 (99.2) | 99.5 (100) | 98.2 (99.5) | 98.2 (99.5) | 99.5 (99.0) |
| Redundancy | 4.0 (4.0) | 3.7 (3.1) | 3.2 (2.4) | 4.2 (4.2) | 2.5 (2.3) | 2.5 (2.3) | 3.8 (3.7) |
| Refinement statistics | | | | | | | |
| Data range (Å) | 50-2.7 | 50-2.6 | 50-2.6 | 50-2.6 | 50-2.8 | 50-2.8 | 50-2.6 |
| Reflections | 52341 | 54635 | 54087 | 61690 | 40031 | 44706 | 60273 |
| Nonhydrogen atoms | 12597 | 12619 | 12558 | 12577 | 12545 | 12535 | 12559 |
| Water molecules | 99 | 111 | 59 | 81 | 46 | 77 | 60 |
| R.m.s. Δ bonds (Å)[b] | 0.6 | 0.6 | 0.7 | 0.6 | 0.6 | 0.5 | 0.6 |
| R.m.s. Δ angles (°)[b] | 0.002 | 0.003 | 0.002 | 0.002 | 0.003 | 002 | 0.002 |
| R-factor (%)[c] | 22.2 | 20.5 | 20.7 | 21.5 | 21.7 | 11.3 | 19.6 |
| Rfree (%)[c,d] | 26.8 | 24.1 | 25.7 | 25.3 | 27.3 | 26.0 | 25.1 |

*Highest resolution shell is shown in parenthesis.

[a]$R_{merge} = 100 \times \Sigma_b \Sigma_i | I_i(h) - <I(h)> | / \Sigma_b <I(h)>$, where $I_i(h)$ is the measurement and $<I(h)>$ is the weight mean of all measurement of I(h) for Miller indices h.

[b]Root-mean-squared deviation (r.m.s. Δ) from target geometries.

[c]R-factor = $100 \times \Sigma |F_f - F_{pscale}| / \Sigma F_p$.

[d]$R_{free}$ was calculated with 5% of the data.

TABLE 2

Data Collection and Refinement Statistics - 4-PBA Crystallography

| COPII protein complex | Sec23/24•22 | Sec23/24•22 | Sec23/24•22 | Sec23/24•22 |
|---|---|---|---|---|
| 4-PBA Concentration | 1 mM | 15 mM | 50 mM | 0 mM |
| Protein Data Bank ID | | | | |
| Space group | C2 | C2 | C2 | C2 |
| Copies/asymmetric unit | 1 | 1 | 1 | 1 |
| Cell parameters: a, b, c (Å) | 147.8, 96.8, 129.6 | 149.1, 96.8, 130.6 | 148.02, 97.7, 128.9 | 148.4, 96.9, 130.5 |
| Ceti parameters: β (°) | 90.2 | 90.2 | 89.6 | 89.6 |
| Data processing | | | | |
| Resolution (Å) | 50-2.4 | 50-2.8 | 50-2.5 | 50-2.9 |
| Rmerge (%)[a] | 8.9(45.9) | 9.9(80.9) | 9.3(56.7) | 7.6(86.2) |
| I/σ | 16.1(1.2) | 11.6(1.2) | 13.3(1.3) | 15.9(1.7) |
| Completeness (%) | 98.9(95.9) | 99.3(99.5) | 99.2(99.1) | 98.6(99.5) |
| Redundancy | 2.9(1.8) | 3.7(3.9) | 3.0(2.3) | 3.6(3.8) |
| Refinement statistics | | | | |
| Data range (Å) | 50-2.4 | 50-2.8 | 50-2.5 | 50-2.9 |
| Reflections | 61011 | 43047 | 53119 | 39048 |
| Nonhydrogen atoms | 12471 | 12462 | 12491 | 12477 |
| Water molecules | 50 | 45 | 59 | 48 |
| R.m.s Δ bonds (Å)[b] | 0.6 | 0.6 | 0.6 | 0.6 |
| R.m.s Δ angles (°)[b] | 0.003 | 0.002 | 0.002 | 0.003 |
| R-factor (%)[c] | 21.1 | 21.3 | 21.2 | 20.9 |
| Rfree (%)[c,d] | 24.6 | 26.0 | 25.1 | 25.3 |

*Highest resolution shell is shown in parenthesis.
[a] $R_{merge} = 100 \times \Sigma_h \Sigma_i | I_i(h) - <I(h)> | / \Sigma_h <I(h)>$, where $I_i(h)$ is the ith measurement and $<I(h)>$ is the weighted mean of all measurement of I(h) for Miller incices h.
[b] Root-mean-squared deviation (r.m.s. Δ) from target geometries.
[c] R-factor = $100 \times \Sigma |F_P - F_{P(calc)}|/\Sigma F_P$.
[d] $R_{free}$ was calcalated with 5% of the data.

Cell Lines and Cell-Based Experiments

T-Rex-CHO-K1 cloned cell lines expressing wild-type and mutant LDL receptor were cultured as described in Sorensen et al. (2006) and Tveten et al. (2007), and according to the manufacturer's protocols (Thermo Fisher Scientific). The expression in CHO cells of G544V-mutant or wildtype LDL receptor protein was induced with 1 μg/mL tetracycline for 24 h prior to experiments with 4-PBA or 4-PBA analogs (Tveten et al. (2007)). To compare pharmacological potency of 4-PBA analogs, cells were incubated with the compounds for 2 hours at 37° C. in 12-well 22 mm plates (Corning Costar #3513). For experiments concerning the extracellular secretion of GRP94 (FIG. 5), the incubations with 4-PBA were extended to 24 hours. Cells were broken in lysis buffer (1% (v/v) Triton X-100, 150 mM NaCl, 10 mM EDTA, 50 mM Tris-HCl pH 7.5) and cleared by centrifugation (15,000 g for 15 minutes). Cellular protein concentration was measured using "Protein Assay Kit II" (Bio-Rad) with bovine serum albumin as standard. Lysates were added to Laemmli sample buffer (New England Bio-Labs) containing 130 mM dithiothreitol and heated for 15 min at 55° C. Cell medium (containing secreted proteins) was added to Laemmli sample buffer containing 5% β-mercaptoethanol and boiled for 5 min. Samples were run on 4-15% Tris/HCl Criterion gels (Bio-Rad) followed by immunoblotting.

Permeabilization of CHO Cells

In vitro COPII budding reactions used permeabilized cells prepared from the T-Rex-CHO-K1 parent line and from the clone that expresses mutant LDL receptor. Permeabilization was carried out as described in Mancias and Goldberg (2008) with modifications. Two culture dishes (150 mm) of cells were prepared with cells at no greater than 60% confluence. Cells were washed with 20 ml PBS at 37° C. and then trypsinized with 2 ml of Trypsin-EDTA (0.05%, Gibco) for 1 min at 37° C.; 100 μl of Soybean Trypsin Inhibitor (2 mg/ml; Sigma) was added to each culture plate. Next, 5.5 ml ice-cold KHM buffer (110 mM KOAc, 20 mM Hepes pH 7.2, 2 mM magnesium acetate) was added per plate, and cells were transferred to a 15 ml Falcon tube and pelleted gently (250 g for 3 min at 4° C.). The supernatant was aspirated and the cells re-suspended in 6 ml ice-cold KHM buffer. To permeabilize the cells, 6 μl digitonin stock solution (40 mg/ml in dimethyl sulfoxide) was added, cells were mixed by inversion and incubated on ice for 5 minutes. To terminate permeabilization, cells were diluted to 14 ml with KHM buffer and immediately pelleted at 250 g for 3 min at 4° C. Cells were re-suspended in 14 ml ice-cold HEPES buffer (50 mM HEPES pH 7.2, 90 mM potassium acetate), incubated for 10 minutes on ice and harvested at 250 g for 3 min at 4° C. Finally, the cells were re-suspended in 1 ml of KCLM buffer (110 mM potassium Chloride, 20 mM HEPES pH 7.2, 2 mM magnesium chloride), harvested at 10,000 g for 15 sec and re-suspended in 60 μl of KCLM buffer. The protein concentration was measured using protein assay kit (Bio-Rad) with BSA as standard; routinely, the measurement is in the range 4-5 mg/ml. Permeabilized cells were used in budding experiments immediately following their preparation.

In Vitro COPII Budding Assay

The COPII vesicle budding assay was carried out as described in Mancias and Goldberg (2008) with minor modifications. Each budding reaction mixture (100 μl) contained 110 mM potassium chloride (chloride was used in place of acetate ions which interfere at the B site), 20 mM HEPES pH 7.2, 2 mM magnesium chloride, protease inhibitor cocktail (1× Roche cOmplete), 0.2 mM GTP, ATP regeneration system (40 mM creatine phosphate, 0.2 mg/ml creatine phosphokinase, 1 mM ATP) and, where indicated, 10 mM 4-PBA. This mixture was brought to 37° C., permeabilized cells (25 μg) were added and the mixture incubated for 1 min at 37° C. The budding reaction was initiated by the addition of coat proteins (2 μg of Sar1a, 2 μg Sec23a/24d or Sec23a/24d-L750W, 4 μg Sec13a/31a) and budding proceeded for 10 min at 37° C. A short budding reaction time was employed to avoid potential contamination of vesicle product with post-ER membranes. Recombinant Sec24d was used for all budding experiments since a sufficiency of Sec23a/24d and Sec23a/24d-L750W proteins, but not of other paralogs, could be prepared for scaled-up budding reactions. Reactions were terminated at 4° C. and centrifuged at medium speed (12,000 g) for 20 min at 4° C. 90 μl of supernatant was transferred to polypropylene centrifuge tubes (Beckman, #343621) and vesicles were pelleted at 55,000 rpm for 35 min at 4° C. in a Beckman TLA 100.1 rotor. To the pellet, 7 μl of lysis buffer (10 mM Tris-HCl pH 7.5, 100 mM NaCl, 1% (v/v) Triton X-100, 300 mM DTT) and 3.5 μl of 3× Laemmli sample buffer were added. The samples were heated at 42° C. for 10 min and 10 μl sample was loaded on 4-20% Tris/HCl Criterion gels (Bio-Rad). Subsequent analysis was carried out by immunoblotting.

Fluorescence Polarization Assay

The fluorescence assay was based on the approach described previously using yeast COPII proteins (Mossessova et al. (2003). A synthetic peptide (sequence QIYTDIEANR (SEQ ID NO: 2)), based on the DxE export signal of VSV G protein, shown previously to bind specifically the B site (Mancias and Goldberg (2008) conjugated at the N terminus with 5-carboxyfluorescein (5-Fam) was purchased from the Tufts University Core Facility (>95% purity); a 250 μM stock solution in Fluor buffer (160 mM NaCl, 50 mM HEPES-NaOH pH 7.5) was stored at −80° C. Stock solutions of 4-PBA analogs (highest purity available) were 714 mM, adjusted to pH 7.5 with NaOH. Fluorescence polarization titrations were performed on a FluoroMax-4 spectrofluorometer with autopolarizer (Horiba Scientific). Excitation and emission wavelengths were set to 490 and 520 nm, respectively, and slits were adjusted to 2 nm to yield approximately $1.5 \times 10^6$ counts during a 0.1 sec signal acquisition with the sample held in a 45 μl cuvette (Hellma analytics cuvette105.251). The affinity between 5-Fam-QIYTDIEANR (SEQ ID NO: 2) and Sec24a was measured by titration as Kd=14.2 μNI. On this basis, competition binding titrations were carried out by maintaining constant concentrations of 5-Fam-QIYTDIEANR (SEQ ID NO: 2) and purified Sec24a (5 μNI and 22 μNI, respectively), while the concentration of the competitor 4-PBA analog was increased in the range 0.2-100 mM to displace the fluorescent peptide. This ratio of fluorescence reporter concentration, Sec24a concentration, and 14.2 μM dissociation constant ensures that the majority of the reporter is bound to Sec24a at the beginning of the titration. The relatively low concentration of Sec24a (~1.5 times the Kd for the reporter) has the effect of reducing the dynamic range of the assay. However, high concentrations of Sec24a would increase the IC50 for all 4-PBA analogs to excessively high values. Under the conditions chosen, the dynamic range is ~100 mP (FIG. 6).

All titrations were carried out at 22° C. in degassed Fluor buffer. Reaction mixtures were incubated at room temperature for 10 minutes then centrifuged at 15,000 g for 10 minutes prior to fluorescent measurement. Positive controls containing free fluorescent reporter without Sec24a (equivalent to 100% inhibition) were included for each titration.

Quantification and Statistical Analysis

Immunoblot Quantification:

Proteins were electrotransferred from SDS-PAGE gels onto Immun-Blot low fluorescence PVDF membrane (Bio-Rad) and blocked using TBST (5% BioRad Blocker in 25 mM Tris-HCl pH 7.4, 150 mM NaCl, 0.05% (v/v) Tween 20). Membranes were incubated at 4° C. overnight with primary antibodies in TBST followed by incubation with horseradish peroxidase-conjugated secondary antibodies. Chemiluminescence signals were generated by incubation with ECL Prime Western Blotting detection reagent (GE Healthcare #RPN2236). High-intensity ECL Select reagent (GE Healthcare #RPN2235) were used for blots from the COPII budding experiments involving ER unstressed cells (FIG. 4) and the analysis was restricted to the highest quality antibodies. Chemiluminescence signals were detected using a ChemiDoc MP Imaging System and acquired with Image Lab 5.0 software (Bio-Rad). Quantification of protein band intensities was performed using Image Gauge software Version 4.1 (Fujifilm), including background correction of the raw image data.

For analysis of COPII budding, the background-subtracted packaging measurements (for p24 proteins, resident proteins and G544V-mutant LDL receptor) were corrected for change in budding yield due to treatment (i.e., 10 mM 4-PBA or mutant COPII protein) using the mean values of the packaging measurements for Syntaxin 5, membrin, Erv46 and Rer1. The datasets in triplicate were placed on a common scale (by minimizing the mean of the ratios of pairwise lane differences). For graphical presentation, the data were then normalized and presented as a percentage of the budding rate due to wild-type COPII coat. All statistical analysis was performed on data prior to normalization in order to preserve statistical distributions.

Figure 6A:
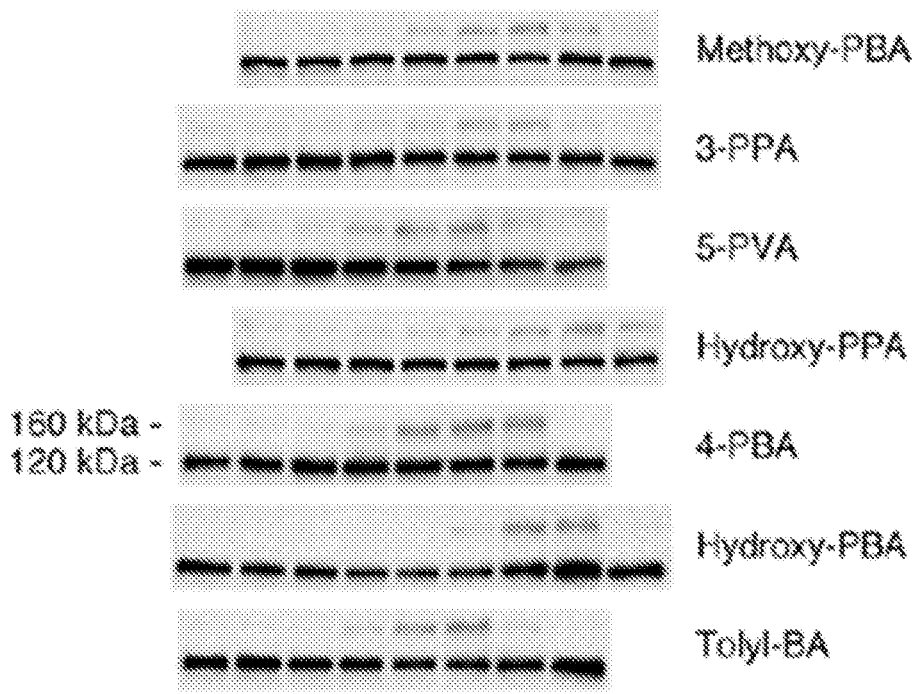
FIG. 6(A) shows CHO cells expressing G544V-mutant LDL receptor that were incubated with the indicated concentrations of 4-PBA analogs for 2 hours at 37° C. Cell lysates were analyzed by immunoblotting for the appearance of 160 kDa mature glycosylated LDL receptor (labeling indicates the position of 160 kDa mature glycosylated and 120 kDa precursor forms of LDL receptor). A gamma correction was applied to improve clarity.
Figure 6B:
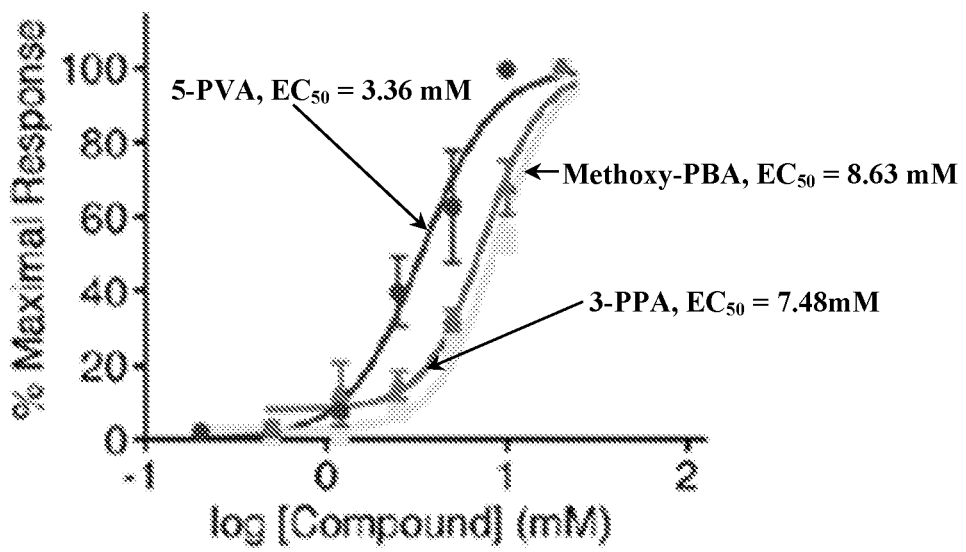
FIG. 6(B) shows a plot depicting the acquisition of mutant LDL receptor glycosylation as a function of compound concentration. EC50 values were reported. Data were obtained from FIG. 6(A) by densitometry of chemiluminescent signals. 4-(4-methoxyphenyl) butyrate (Methoxy-PBA) (n=4 independent experiments); 3-phenylpropionate (3-PPA) (n=4); and 5-phenylvalerate (5-PVA) (n=5). Standard errors for EC50 values are reported in General Methods described herein.
Figure 6C:
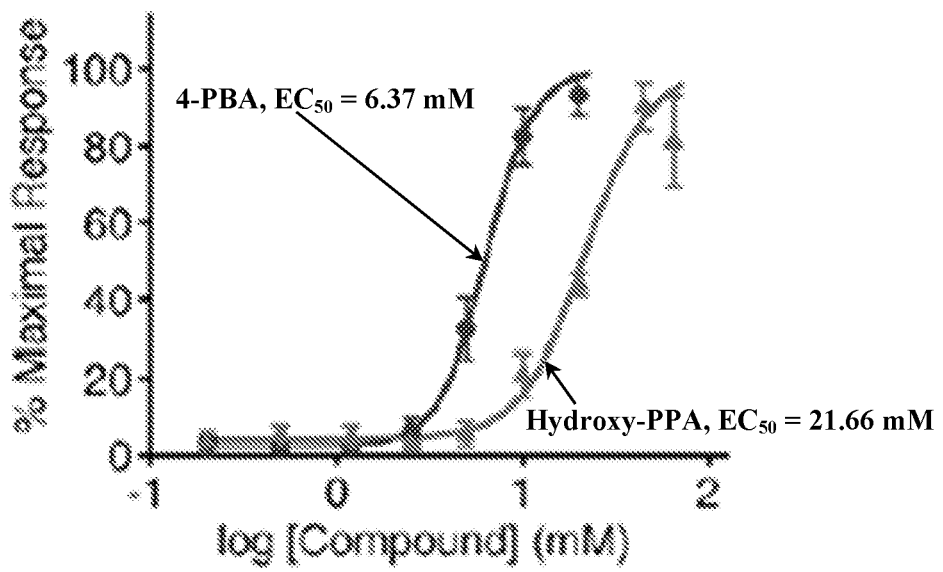
FIG. 6(C) shows a plot depicting the acquisition of mutant LDL receptor glycosylation as a function of compound concentration. EC50 values were reported. Data were obtained from FIG. 6(A) by densitometry of chemiluminescent signals. 3-(4-hydroxyphenyl) propionate (Hydroxy-PPA) (n=4); 4-PBA (n=5). Standard errors for EC50 values are reported in General Methods described herein.
Figure 6D:
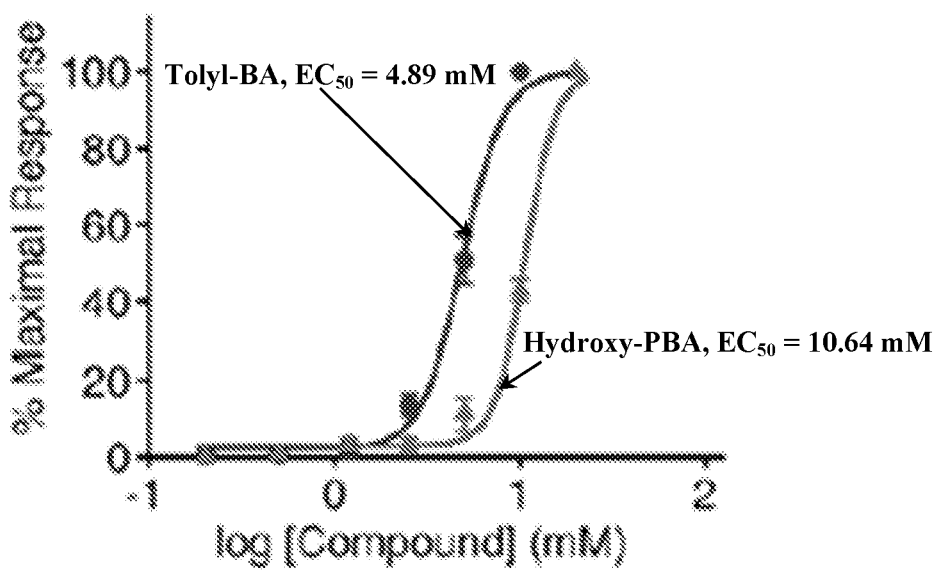
FIG. 6(D) shows a plot depicting the acquisition of mutant LDL receptor glycosylation as a function of compound concentration. EC50 values were reported. Data were obtained from FIG. 6(A) by densitometry of chemiluminescent signals. 4-(4-hydroxyphenyl) butyrate (Hydroxy-PBA) (n=4); 4-(4-tolyl) butyrate (Tolyl-BA) (n=4). Standard errors for EC50 values are reported in General Methods described herein.
Figure 6E:
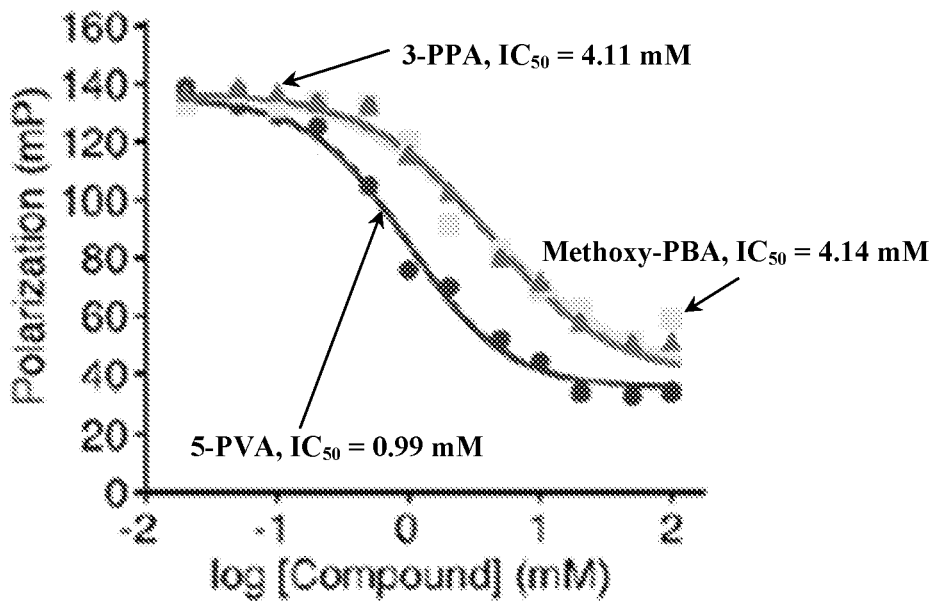
FIG. 6(E) shows a graph depicting the displacement of the fluorescent probe 5-Fam-QIYTDIEANR (SEQ ID NO: 2) (based on the ER export signal of VSV G protein) from human Sec24a by methoxy-PBA and 3-PPA as measured by fluorescence polarization at 22° C. IC50 values were determined by non-linear regression fitting (standard errors are reported in General Methods described herein).
Figure 6F:
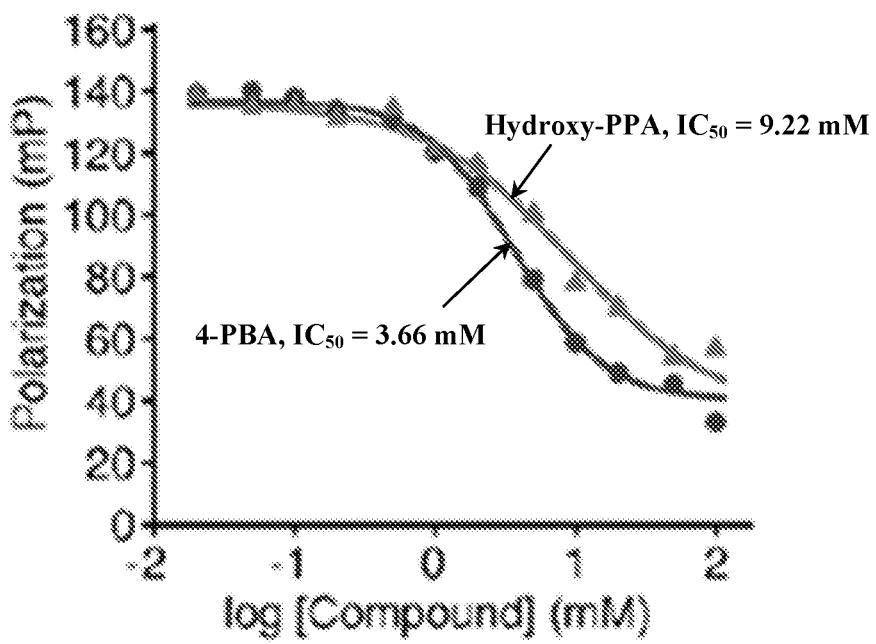
FIG. 6(F) shows a graph depicting the displacement of the fluorescent probe 5-Fam-QIYTDIEANR (SEQ ID NO: 2) (based on the ER export signal of VSV G protein) from human Sec24a by hydroxy-PPA and 4-PBA as measured by fluorescence polarization at 22° C. IC50 values were determined by non-linear regression fitting (standard errors are reported in General Methods described herein).
Figure 6G:
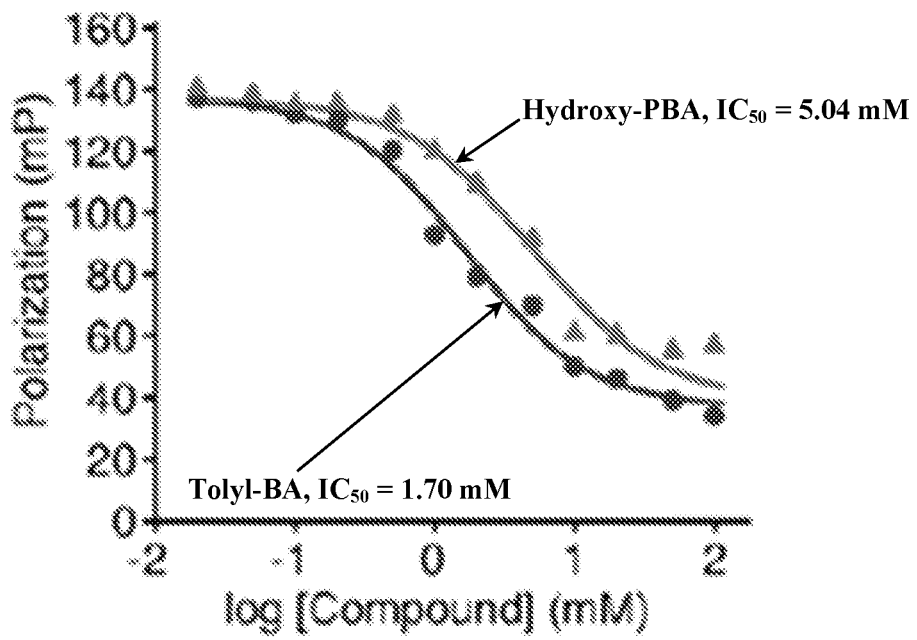
FIG. 6(G) shows a graph depicting the displacement of the fluorescent probe 5-Fam-QIYTDIEANR (SEQ ID NO: 2) (based on the ER export signal of VSV G protein) from human Sec24a by hydroxy-PBA and tolyl-BA as measured by fluorescence polarization at 22° C. IC50 values were determined by non-linear regression fitting (standard errors are reported in General Methods described herein).

Binding Analysis for 4-PBA Ligands:

Chemiluminescence signals from western blots for the glycosylated (160 kDa) form of G544V mutant LDL receptor were quantified as a percentage of total LDL receptor protein (glycosylated+unglycosylated bands). Data at high concentrations of 4-PBA analogs, which show inhibition of LDL receptor trafficking, were omitted. Data from individual experiments were normalized (to obtain maximal response=100%), so that data from replicate experiments (n=4-5) could be averaged. Logistic fitting to the dose-response data was carried out with program Ultrafit (Elsevier Biosoft). The EC50 values and associated standard errors for the fits shown in FIGS. 6(B)-6(D) are as follows: Methoxy-PBA, 8.63±0.98 mM; 3-PPA, 7.48±0.68 mM; 5-PVA, 3.36±0.42 mM; Hydroxy-PPA, 21.66±1.03 mM; 4-PBA, 6.37±0.50 mM; Hydroxy-PBA, 10.64±0.40 mM; Tolyl-BA, 4.89±0.24 mM. Data from fluorescence polarization titrations (FIGS. 6(E)-6(G)) were analyzed with Ultrafit, and IC50 values were determined from plots using nonlinear curve fitting. The IC50 values and associated standard errors for the fits in FIGS. 6(E)-6(G) are as follows: Methoxy-PBA, 4.14±0.70 mM; 3-PPA, 4.11±0.34 mM; 5-PVA, 0.99±0.08 mM; Hydroxy-PPA, 9.22±0.94 mM; 4-PBA, 3.66±0.22 mM; Hydroxy-PBA, 5.04±0.69 mM; Tolyl-BA, 1.7±0.16 mM. IC50 values were converted to true affinities, Ki, using the approach of (Nikolovska-Coleska et al., 2004), and these are used in the scatter plot, FIG. 6(H).

Statistics:

All instances of replicate measurements are biological replicates; that is, they are measurements of biologically distinct samples. For analysis of COPII budding experiments, chemiluminescent densitometry data were assembled in Excel and group means were compared by one-way ANOVA. A post-hoc Bonferroni-Holm test was used to control the experiment-wise error rate for a subset of the pairwise comparisons, specifically the cargo-packaging rate due to COPII relative to 4-PBA treatment or to mutant- COPII treatment. The 50/50 (wild-type/mutant) COPII mix was used in budding experiments merely to emulate the effect of 10 mM 4-PBA; this mix has a partial effect on cargo packaging, with reduced statistical power relative to 100% mutant COPII, hence these data were excluded from statistical analysis.

Figure 6H:
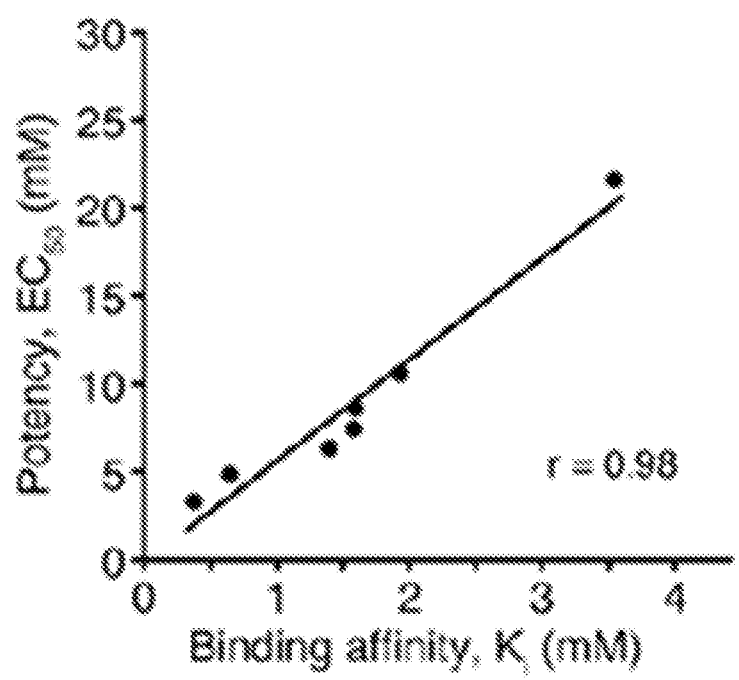
FIG. 6(H) shows a scatter plot comparing data from the cell-based and fluorescence polarization experiments. For the latter, IC50 values were converted to true affinities, Ki, using the approach of (Nikolovska-Coleska et al. (2004).

As reported in FIG. 6(H), the comparison between COPII binding-site affinity and pharmacological potency for the series of 4-PBA analogs yields a linear correlation coefficient r(5)=0.98; this is significant at P<0.0005 for a two-tailed test.

Example 1—Binding Site on COPII Protein for ER Export Signals Containing the ΦC Motif This example demonstrates that ER export by the COPII mechanism requires a signal having the ΦC motif.

Methods

A series of ΦC-signal peptides were synthesized, based on a core sequence of yeast Emp24p, and individual peptides were soaked at high concentrations into two crystal forms of human COPII protein: one comprising Sec23a/Sec24a•Sec22b, the other Sec24c. X-ray diffraction data was collected from cryopreserved crystals (see General Methods). For all ΦC sequences, it was observed that the peptides were binding to a site on Sec24a in the Sec23a/Sec24a•Sec22b crystals, based on the presence of residual electron density that matches the peptide sequence (this binding site is occluded in the Sec24c crystals). FIGS. 1(A)-1(E) show four of the COPII•ΦC crystal structures (additional structures are presented in FIGS. 7(A)-7(F); X-ray crystallography statistics and ΦC peptide sequences are reported in Table 1).

Results

The COPII•ΦC crystal structures (FIGS. 1(A)-1(E) and 7(A)-7(F)) highlight that the common molecular feature is carboxylate-group recognition by the clustered arginine residues of the B site—the terminal carboxylate group of the ΦC motif adopts a similar position and bonding arrangement to the carboxylate of the glutamate side chains of LxxLE and DxE motifs (FIGS. 7(A)-7(F)). The specific recognition of the ΦC motif involves the terminal carboxylate group bonding to Arg750 and Arg752 of Sec24a, with the penultimate hydrophobic residue of the motif nestling against Tyr496, and the terminal hydrophobic residue fitting to a pocket of hydrophobic side chains (FIGS. 1(B)-1(E) and 7(A)-7(F)). These molecular features were in concordance with functional data concerning ΦC motifs as ER export signals (Nakamura et al. (1998); Nufer et al. (2002)). The B-site hydrophobic pocket accommodates a range of hydrophobic side chains; however, a terminal valine is the most favored residue because its fit to the pocket allows optimal geometry for bonding to the terminal carboxylate group (shown schematically in FIG. 1(D)). A subtle change of the bonding geometry was observed for the Phe-Phe motif of ERGIC-53, in which the larger terminal side chain of phenylalanine was accommodated by a shift of the carboxylate group to bond Arg750 in a bidentate fashion (FIG. 1(E)).

These results show that the COPII mechanism requires a signal having the ΦC motif.

Example 2—4-PBA Mimics the CPC Signal Motif to Bind to COPII

This example demonstrates that 4-PBA mimics the ΦC signal motif and binds to COPII.

Methods

Crystals of Sec23a/Sec24a•Sec22b were equilibrated with solutions containing 4-PBA at concentrations of 1, 15 and 50 mM (see General Methods and Table 2).

Results

Figure 1A:
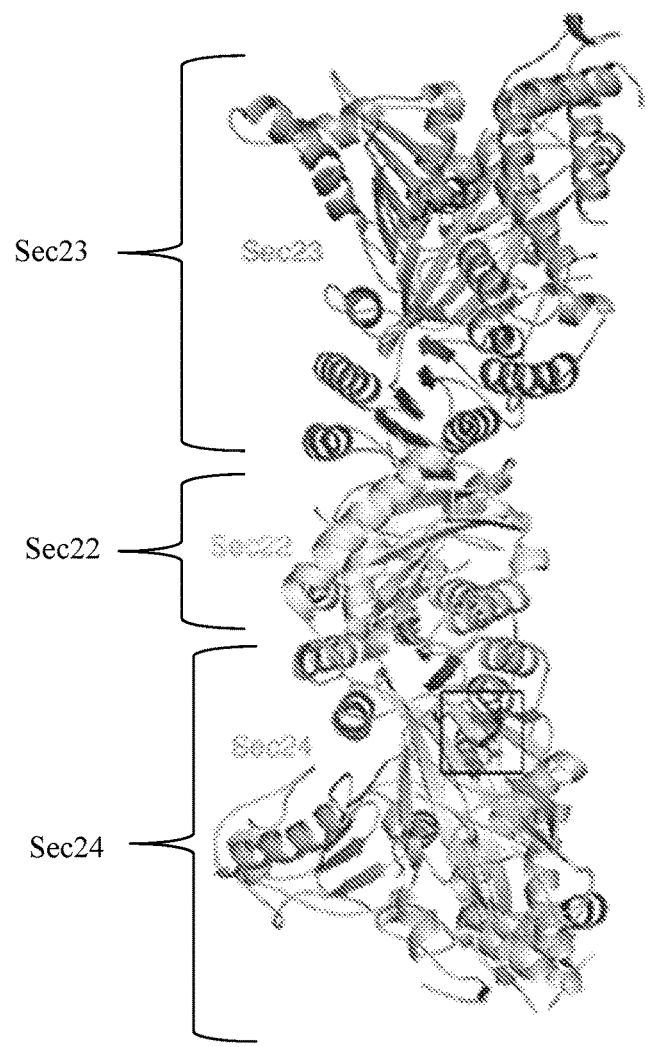
FIG. 1(A) shows a crystal structure of the COPII•SNARE complex comprising human Sec23a/Sec24a•Sec22b bound to a ΦC peptide (boxed).
Figure 1B:
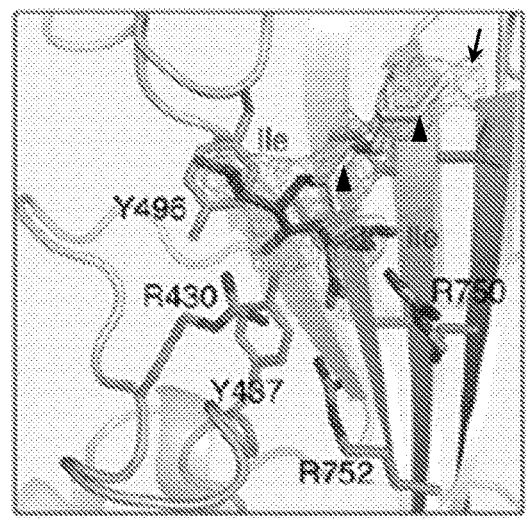
FIG. 1(B) shows a structure of the B site on Sec24a with bound ΦC sequence containing the terminal Ile-Ile motif of the S. cerevisiae p24 protein Erv25p. Contour lines (arrow) show residual electron density ($F_o$-$F_c$ synthesis with no phase bias) at 2.6 Å resolution, contoured at 2.6σ. Electron density was also observable for N-terminal residues of the peptide (arrowheads). Key side chains of Sec24 are labeled (e.g., Y496, R430, Y437, R752 and R750). See Table 1 for details of peptide-bound crystal structures.
Figure 1C:
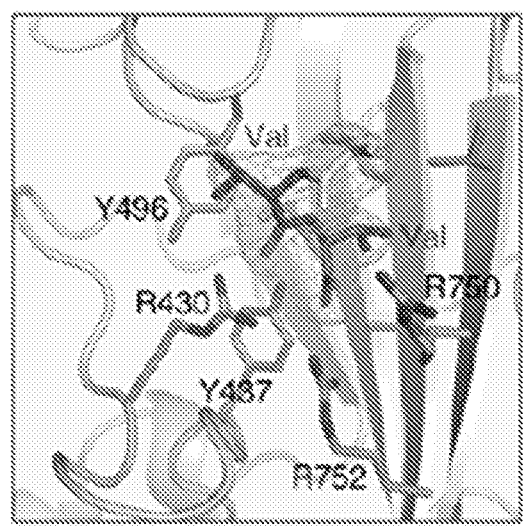
FIG. 1(C) shows a structure showing the residual ($F_o$-$F_c$) electron density (2.6 Å resolution, 2.6σ contour) for a bound ΦC peptide containing the terminal Val-Val motif of human p24β1.
Figure 1D:
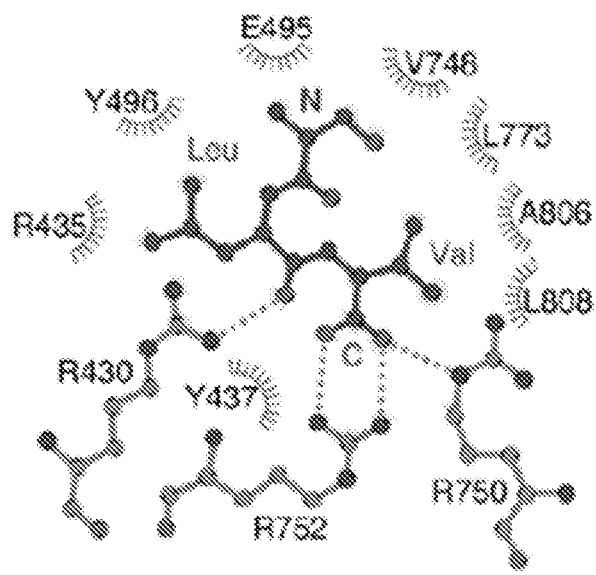
FIG. 1(D) shows a schematic diagram showing the bonding arrangement to the potent ΦC motif Leu-Val (center). Diagram is based on the structure of Sec23a/Sec24a•Sec22b bound to the sequence EVTSLV (SEQ ID NO. 1) (see Table 1). The label N denotes the serine residue upstream of the Leu-Val motif.
Figure 1E:
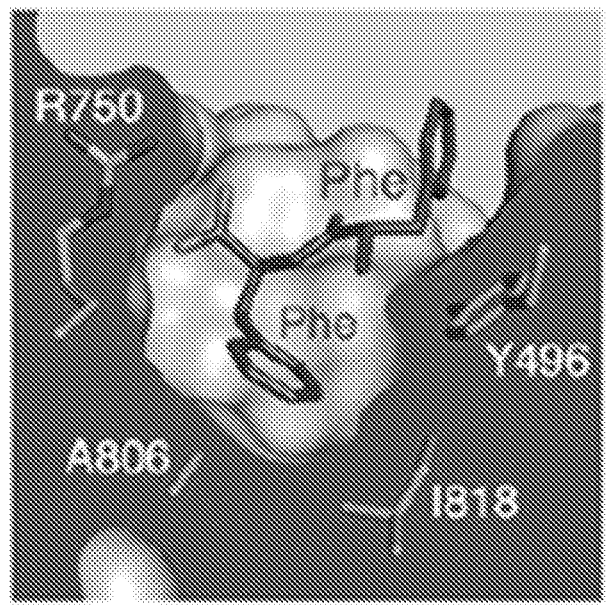
FIG. 1(E) shows a structure showing the conformation of a ΦC peptide containing the terminal Phe-Phe motif of ERGIC-53 bound to Sec24a (drawn as a surface representation).
Figure 1F:
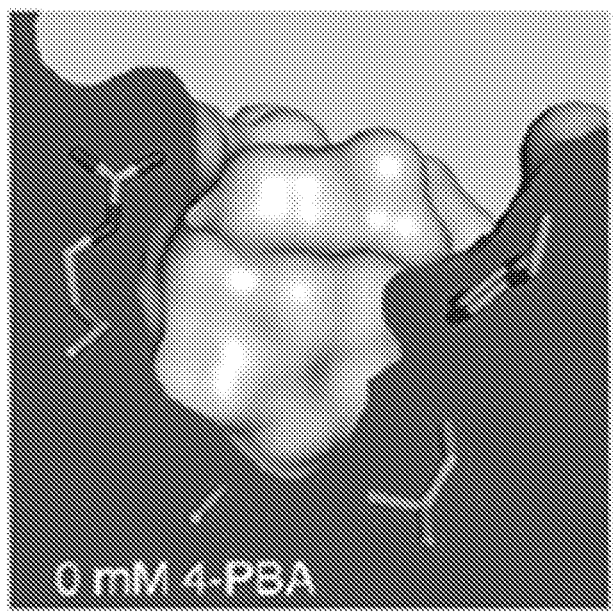
FIG. 1(F) shows a structure showing the residual ($F_o$-$F_c$) electron density (2.8 Å resolution, 2.3σ contour, no phase bias) at the B site for crystals soaked at 0 mM 4-PBA. No electron density is observable for ordered water or solute molecules at this contour level in the 0 mM 4-PBA. The electron density calculations are all truncated at 2.8 Å; see Table 2 for details of X-ray datasets.
Figure 1G:
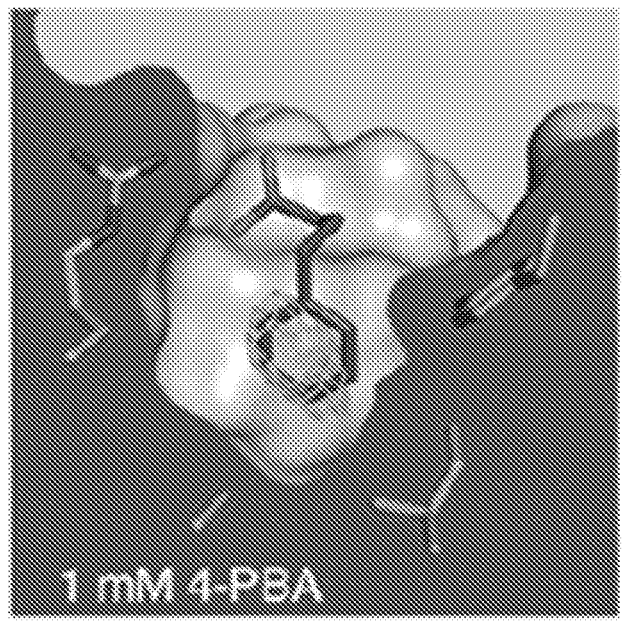
FIG. 1(G) shows a structure showing the residual ($F_o$-$F_c$) electron density (2.8 Å resolution, 2.3σ contour, no phase bias) at the B site for crystals soaked in 4-PBA at 1 mM 4-PBA. The electron density calculations are all truncated at 2.8 Å; see Table 2 for details of X-ray datasets.
Figure 1H:
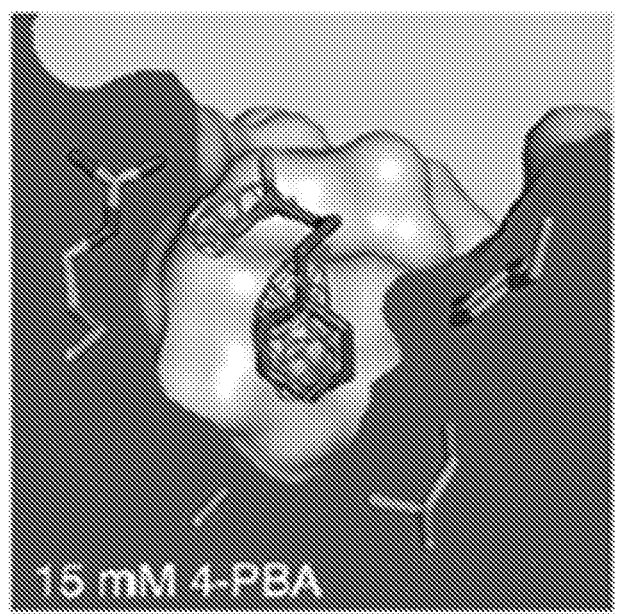
FIG. 1(H) shows a structure showing the residual ($F_o$-$F_c$) electron density (2.8 Å resolution, 2.3σ contour, no phase bias) at the B site for crystals soaked in 4-PBA at 15 mM 4-PBA. The electron density calculations are all truncated at 2.8 Å; see Table 2 for details of X-ray datasets.
Figure 1I:
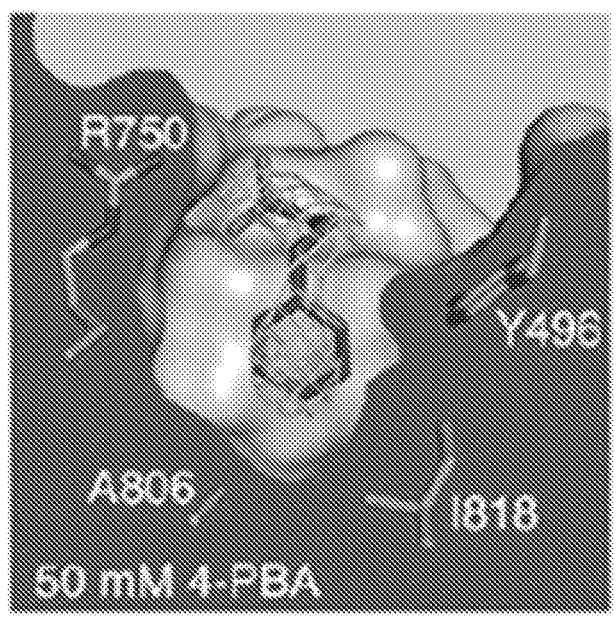
FIG. 1(I) shows a structure showing the residual ($F_o$-$F_c$) electron density (2.8 Å resolution, 2.3σ contour, no phase bias) at the B site for crystals soaked in 4-PBA at 50 mM 4-PBA. The electron density calculations are all truncated at 2.8 Å; see Table 2 for details of X-ray datasets.

Difference Fourier maps calculated from X-ray diffraction data show clear evidence for binding of 4-PBA to the B site of Sec24a (FIGS. 1(F)-1(I)). 4-PBA closely mimics the terminal phenylalanine side chain and carboxylate group of the Phe-Phe motif of ERGIC-53 (compare FIGS. 1(E) and 1(I)). The residues contacting 4-PBA are almost invariant among the four human Sec24 paralogs; only Sec24a residue I818 (drawn in FIG. 1(I)) varies, and the change is a conservative one to leucine in Sec24c/d.

These results show that 4-PBA mimics the ΦC signal motif and binds to COPII.

Example 3—Vesicle Packaging of p24 Proteins is Inhibited by 4-PBA and by a CPC Binding-Site Mutation This example demonstrates that p24 proteins are captured into vesicles by the B site of COPII and that the B site of COPII is targeted by 4-PBA.

Methods

Figure 2A:
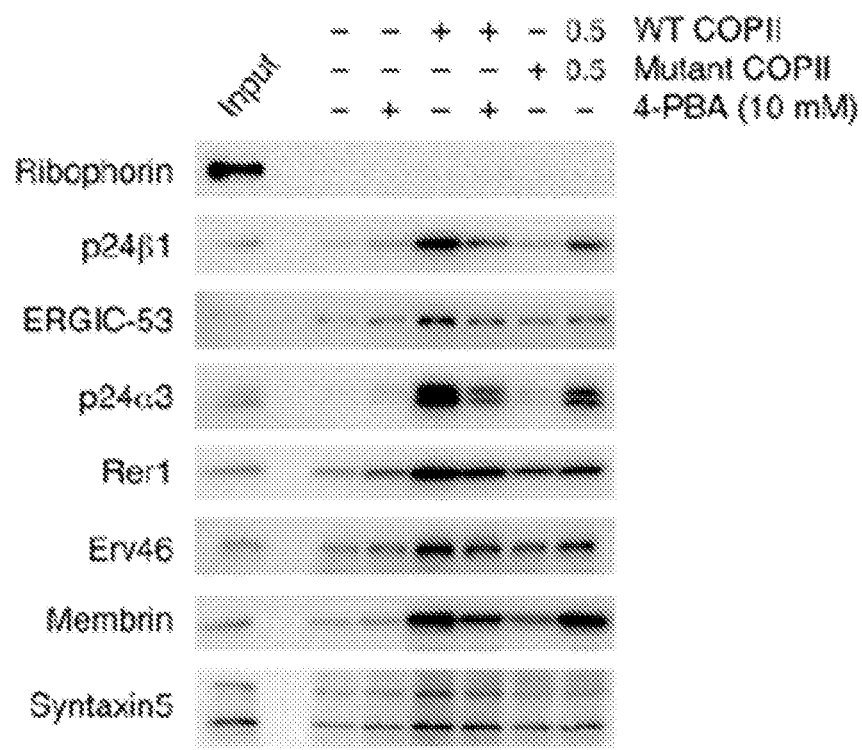
FIG. 2(A) shows reconstituted COPII budding reactions that were performed using permeabilized CHO (T-Rex-CHO-K1) cells, with either wild-type or mutant (Sec24d-L750W) COPII protein. Protein contents of the isolated vesicles were analyzed by immunoblotting. The lane labeled Input represents 1.1% of the starting permeabilized cell membranes used in a budding reaction; all other lanes represent the vesicle product of 100% of the starting membranes. The syntaxin 5 antibody recognizes both the short and long forms of the SNARE protein. These are representative blots from experiments performed in triplicate.
Figure 2B:
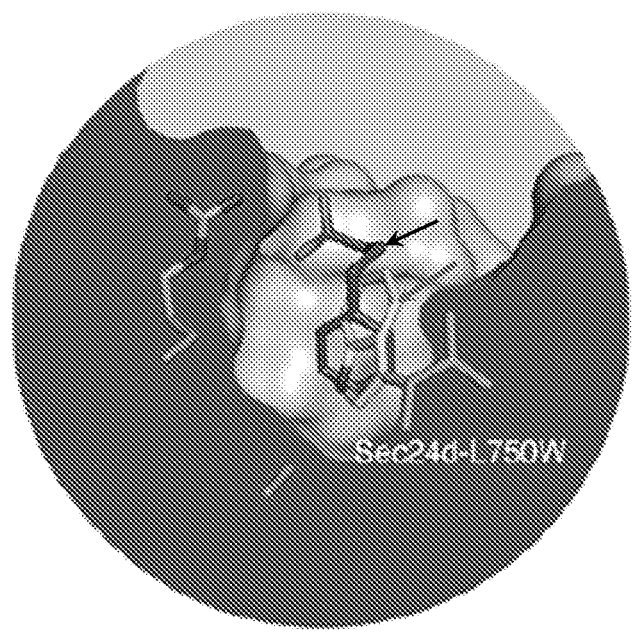
FIG. 2(B) shows a structure showing the B site of Sec24d, oriented as in FIGS. 1(E)-1(I), showing 4-PBA (black arrow) and a modeled position of the tryptophan side chain (gray arrow) in the Sec24d-L750W mutant protein used in budding reactions.
Figure 2C:
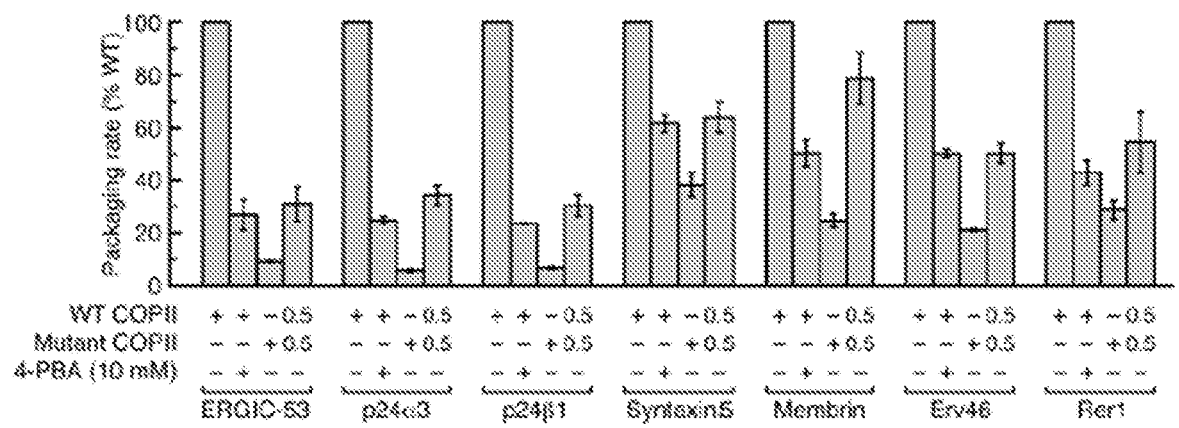
FIG. 2(C) shows a graph depicting the packaging rate for cargo proteins as determined by immunoblotting as in FIG. 2(A) and densitometry of chemiluminescent signals. For each cargo molecule, data was normalized to be a percentage of the packaging rate measured using wild-type COPII protein. Bar graphs show mean±s.e.m. (n=3).
Figure 2D:
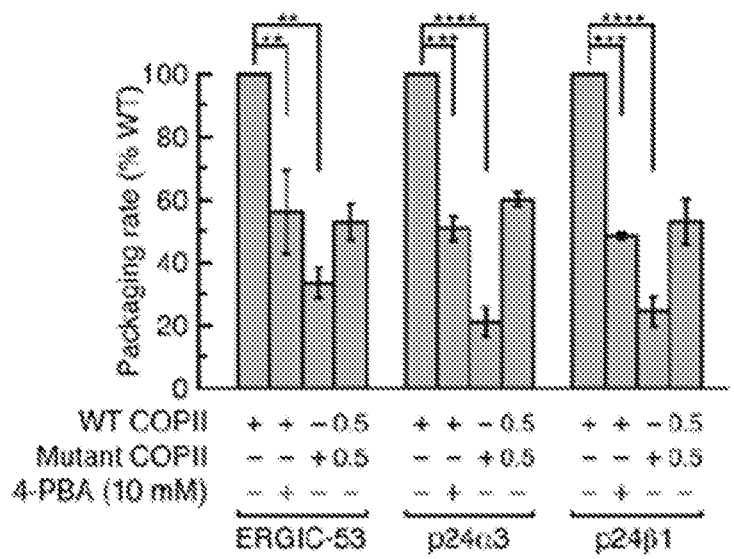
FIG. 2(D) shows data in FIG. 2(C) was corrected for treatment-dependent (4-PBA or mutant COPII) changes in budding yield (using the mean values of the packaging rates for Syntaxin 5, membrin, Erv46 and Rer1). For clarity, data was normalized as in FIG. 2(C). Statistical analysis was performed on data prior to normalization in order to preserve statistical distributions (n=3; ANOVA test, Bonferroni-Holm post hoc, $P<0.01$, *$P<0.001$ and ****$P<0.0001$). Bar graphs show mean±s.e.m.

A mammalian permeabilized cell assay that measures the selective packaging of cargo proteins into COPII-coated vesicles was used to measure the packaging of a series of cargo proteins into vesicles budded from permeabilized CHO (T-Rex-CHO-K1) cells (see FIGS. 2(A) and 2(C)-2(D)) (see General Methods). Vesicle budding was supported in the assay by purified recombinant COPII coat proteins (Sec23/24, Sec13/31 and Sar1), or mutants thereof, in the absence of cytosol.

To test the role of the B site in packaging p24 and ERGIC-53 proteins, the mutation L750W was introduced into Sec24d. The Sec24d-L750W mutation (see FIG. 2(B)) was a tryptophan side chain that is restricted to a single rotamer, and this conformation blocks binding of all ligands to the B site. This mutation was designed previously for a study of yeast COPII (Miller et al. (2003)), where it was reported that the corresponding Sec23/Sec24-L616W mutant protein lost all ability to package LxxLE- and DxE-signal cargoes, and exhibited reduced packaging efficiency of Erp1p (a p24 protein) and Emp47p (yeast ERGIC-53 homolog); COPII-coated vesicles budded with the mutant protein exhibited negligible differences in size and morphology when compared to wild-type vesicles (Miller et al. (2003)).

Results

Cargo packaging was efficient (Table 3) and COPII-dependent. The translocon accessory protein Ribophorin I was absent from all vesicle fractions, indicating that ER membrane integrity was preserved.

TABLE 3

Cargo packaging efficiency measured for wild-type COPII protein

| | Packaging efficiency (Amount in vesicle as % of protein present in starting permeabilized cells) | |
|---|---|---|
| | CHO-LDLR$_{G544V}$ cells | Wild-Type CHO cells |
| Cargo | | |
| ERGIC-53 | 4.5 | — |
| p24δ1 | 7.7 | 4.6 |
| p24α2 | 8.7 | 10.9 |
| p24β1 | 10.6 | — |
| p24α3 | 6.4 | 6.4 |
| Syntaxin 5 | 0.89 | 0.96 |
| Membrin | 4.8 | — |
| Erv46 | 6.6 | 3.9 |
| Rer1 | 11.5 | 5.4 |
| ER resident | | |
| Calnexin | 0.32 | 0.065 |
| ERp57 | 0.63 | 0.12 |
| BiP | 0.87 | — |
| GRP94 | 0.25 | 0.07 |

As seen in FIGS. 2(A) and 2(C), the uptake of p24 proteins (p24α3 and p24β1) and ERGIC-53 into vesicles by Sec23a/24d-L750W mutant COPII was substantially reduced to about 5-8% of that obtained with wild-type COPII.

The total yield of COPII vesicles was significantly lower for the mutant coat, which was likely due to the decreased number of contacts made between coat protein and transmembrane cargo, a phenomenon reported previously for mammalian and yeast COPI-coated vesicles (Bremser et al. (1999); Sandmann et al. (2003)).

To control for the change in budding yield, the packaging rates of four proteins that do not bind the B site was measured (FIG. 2(A)): the recycling receptors Erv46 and Rer1, and the SNARE proteins Syntaxin 5 and Membrin (GS27) that utilize a distinct IxM motif for binding Sec24d. The uptake into vesicles was highly correlated for these four cargoes (see FIG. 2(C)), and the packaging rates for p24 proteins were corrected on this basis (see Quantitation and Statistical Analysis in General Methods).

The blockade of the B site in Sec24d-L750W reduced the packaging rate of p24α3 and p24β1 to 20-25% of the wild-type level (FIG. 2(D)). This residual p24 packaging was at a similar level to that reported for yeast B-site-mutant COPII (Miller et al. (2003)), which indicates that it constitutes the bulk flow (passive) level of uptake of these proteins.

When COPII vesicles were budded in the presence of 10 mM 4-PBA, a 50% reduction in the packaging rate of p24 proteins and ERGIC-53 was observed (FIGS. 2(A) and 2(D)). This concentration of 4-PBA was slightly above its EC50 of 6.4 mM as measured in a cell-based transport assay (see FIG. 3(B)).

It was assessed whether the effects of 10 mM 4-PBA on cargo packaging were consistent with a partial occupancy of the B site, as emulated by a 50/50 mixture of wild-type and mutant COPII proteins. FIGS. 2(A) and 2(C) show that the effects of the two treatments on the seven cargo proteins were qualitatively and quantitatively highly similar.

Together with the crystallographic observations (see Examples 1 and 2), the results show that the packaging of p24 proteins into COPII vesicles involves an interaction of the ΦC motif with the B site of Sec24, and that 4-PBA competes directly with p24 proteins to bind this site. The results show that the ΦC motif and 4-PBA molecule bind to Sec24a (by crystallographic analysis) and to Sec24d (budding experiments). Accordingly the results show that COPII vesicles package p24 proteins to high levels because all paralogs of Sec24 can bind the ΦC motif, and that all are targets of 4-PBA.

Example 4—4-PBA Promotes COPII Packaging of Resident Proteins and ER-Trapped Mutant LDL Receptor This example demonstrates that treatment with 4-PBA resulted in a defect in ER retention and caused packaging of resident and misfolded proteins.

Methods

A system comprising a CHO (T-Rex-CHO-K1) cell clone expressing the G544V-mutant human LDL receptor under a tetracycline-inducible promoter was used (see General Methods) to measure the packaging of resident proteins and a misfolded mutant LDL receptor into COPII vesicles budded from permeabilized cells. The G544V-mutant human LDL receptor is a naturally occurring transport-defective (class 2) mutant LDL receptor with a point mutation in the luminal β-propeller domain that causes ER trapping with chaperone association. 4-PBA has been show to restore transportation of G544V-mutant human LDL receptor to the plasma membrane (Tveten et al. (2007)).

Results

Figure 3A:
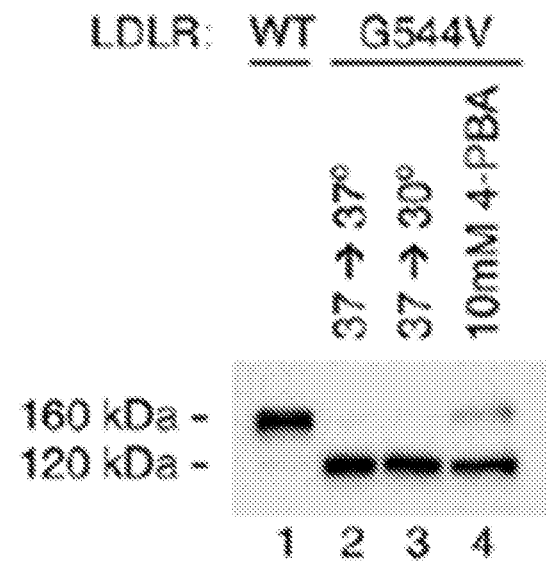
FIG. 3(A) demonstrates that the G544V-mutant LDL receptor failed to reach the Golgi complex. CHO cells stably transfected with wild-type (lane 1) or mutant LDL receptor were induced with tetracycline for 24 hours at 37° C. before further incubation for 2 hours at 37° C. (lane 2) or 30° C. (lane 3), or 2 hour incubation at 37° C. with 10 mM 4-PBA (lane 4). Cell lysates were analyzed by immunoblotting; labeling indicates the 160 kDa mature glycosylated and 120 kDa precursor forms of LDL receptor.

It was verified that the mutant LDL receptor is not thermoreversible, since there was no evidence for transport to the Golgi complex during a 2 hr temperature shift of the cells to 30° C. (FIG. 3(A); transport to the Golgi is monitored by the acquisition of Golgi-specific glycosylation to yield a 160 kDa form). It was also observed that application of 10 mM 4-PBA to cells restored the trafficking of as much as 25% of the receptor (FIG. 3(B)), in line with the results reported in Tveten et al. (2007).

Figure 3B:
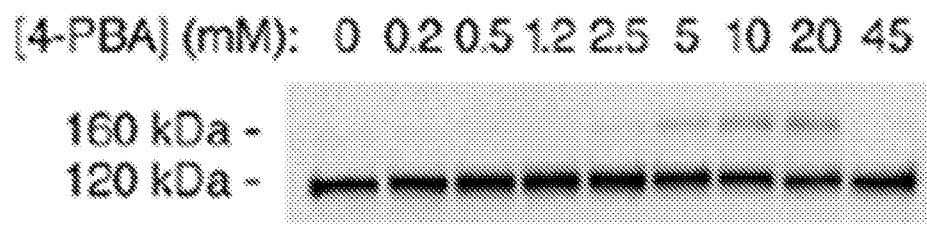
FIG. 3(B) shows dose-dependent restoration of trafficking of mutant LDL receptor by 4-PBA. CHO cells expressing mutant LDL receptor were incubated with indicated concentrations of 4-PBA for 2 hours at 37° C. Cell lysates were analyzed as in FIG. 3(A).
Figure 3C:
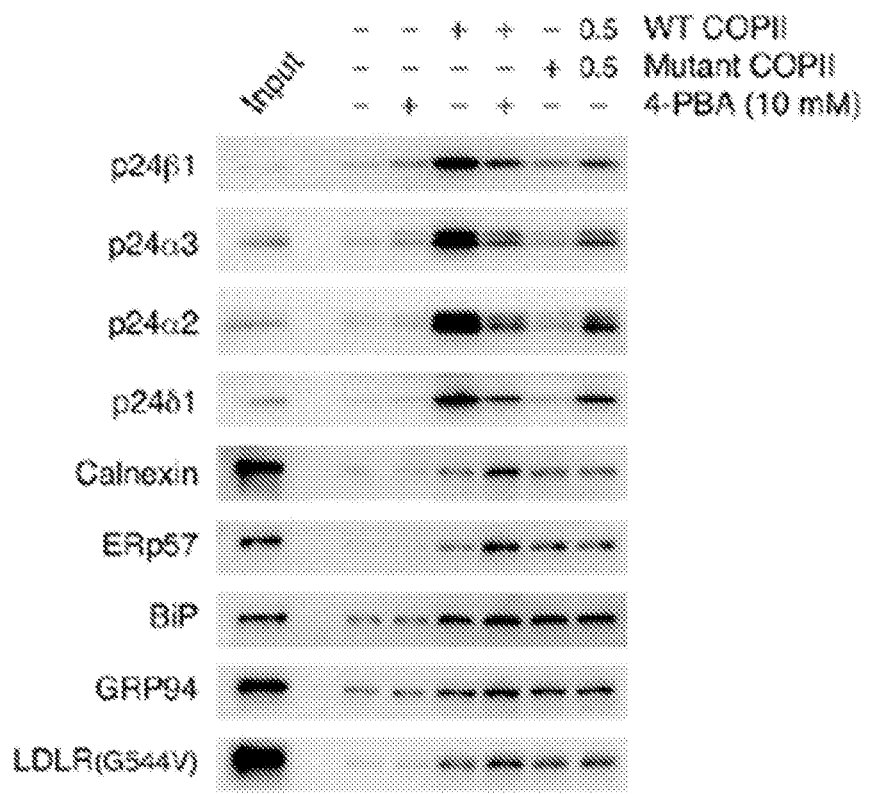
FIG. 3(C) shows the packaging of a series of p24 proteins, ER resident proteins and mutant LDL receptor that were assayed in scaled-up COPII budding reactions. The lane labeled Input represents 1.1% of the starting membranes; all other lanes represent the vesicle product of 100% of the starting membranes. Experiments were performed in triplicate.
Figure 3D:
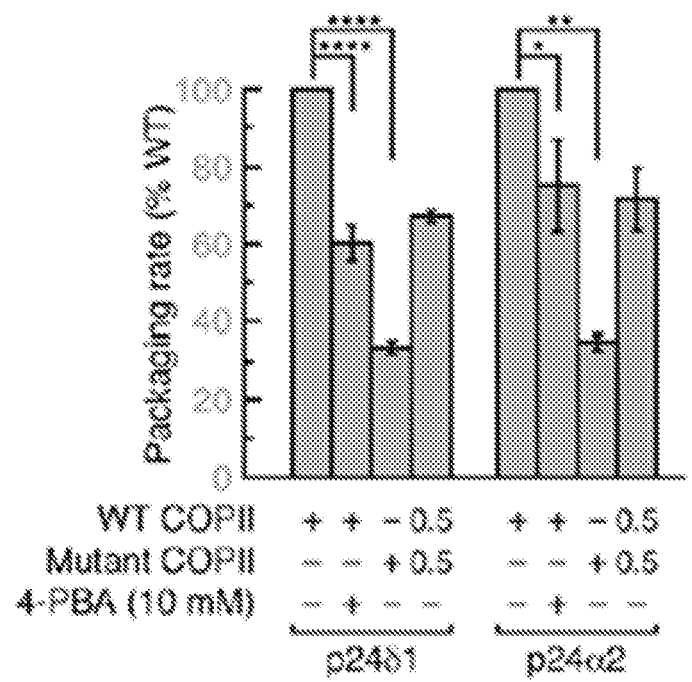
FIG. 3(D) shows a graph depicting the packaging rates for the p24-family proteins p24δ1 and p24α2, similar to that presented in FIG. 2(D) (controlled by Syntaxin 5, membrin, Erv46 and Rer1 packaging rates). The data for p24α3 and p24β1 are in FIG. 2(D) (n=3; ANOVA test, Bonferroni-Holm post hoc, *$P<0.05$, $P<0.01$ and **$P<0.0001$). Bar graphs show mean±s.e.m.
Figure 3E:
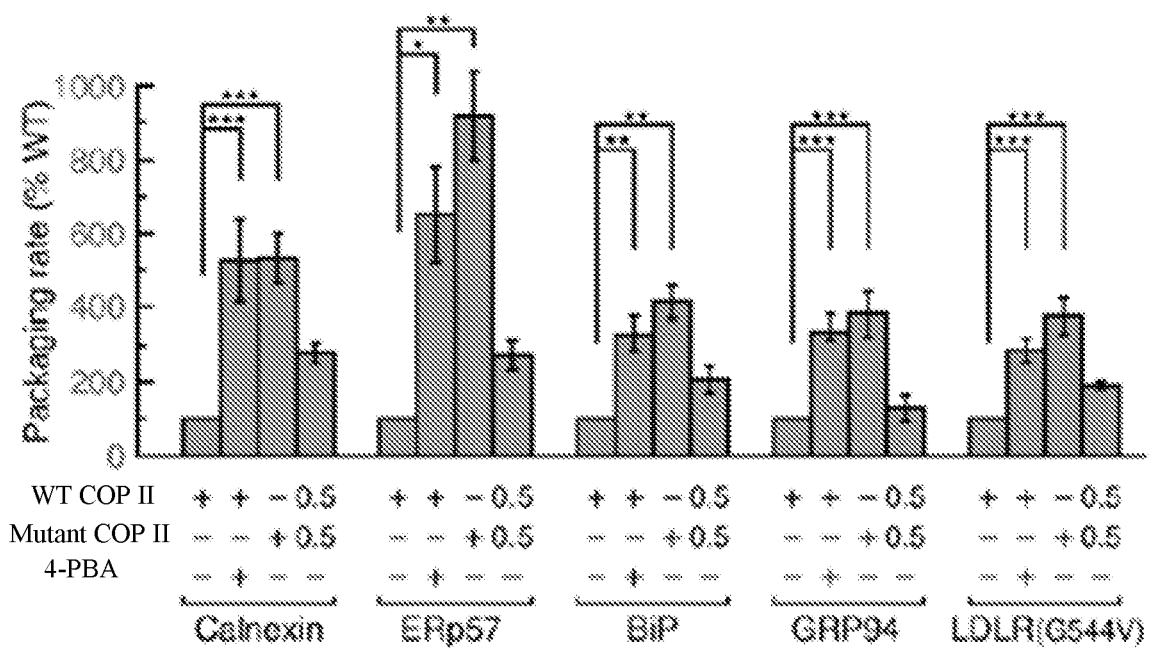
FIG. 3(E) shows a graph showing packaging rates for four ER resident proteins and mutant LDL receptor. The change of scale of the y-axis (n=3; ANOVA test, Bonferroni-Holm post hoc, *$P<0.05$, $P<0.01$ and *$P<0.001$). Bar graphs show mean s.e.m.

FIG. 3(C) shows the results of a COPII budding experiment in which the packaging of a series of p24 proteins, ER residents and G544V-mutant LDL receptor were probed. The depletion from vesicles of p24 proteins caused by 10 mM 4-PBA and by B-site mutation is accompanied by a significant enrichment of residents and mutant LDL receptor (see FIG. 3(C); FIGS. 3(D)-3(E) show the packaging rates corrected for change in budding yield). Vesicles budded with B-site-mutant COPII package five times as much calnexin as wild-type vesicles; the enrichment factors for BiP, GRP94, and mutant LDL receptor were all approximately 4-fold, and the protein disulfide isomerase ERp57 (PDIA3) was enriched 9-fold (FIG. 3(E)).

Measurements taken from the same vesicle pools for four p24 proteins showed on average a 3.5-fold depletion (FIGS. 2(D) and 3(D)). The protein sorting by the COPII coat yields a 15- to 25-fold purification of p24 proteins from ER residents—purification here refers to the product of resident-protein depletion and p24 enrichment in wild-type vesicles relative to B-site-mutant vesicles. Note that the degree of purification was inherent to the raw data in FIG. 3(C); i.e., it was unaffected by the corrections for changes in budding yield that are made for data presentation in FIGS. 2(D) and 3(D)-3(E).

The results show that resident-protein complexes are sufficiently small to be packaged into mutant and 4-PBA-treated COPII vesicles. The results also show that the observed reciprocal relationship between packaging of p24 proteins and residents was consistent with the model of an active sorting mechanism involving p24-dependent exclusion of diffusible resident-protein complexes.

Example 5—Protein Sorting by COPII Vesicles Reconstituted Using ER Unstressed Cells This example demonstrates that the COPII coat is capable of sorting resident proteins from cargo in the context of ER unstressed cells.

Methods

Reconstituted COPII budding reactions were performed on permeabilized CHO cells that were expressing neither wild-type nor mutant LDL receptor (see General Methods).

Results

Figure 4A:
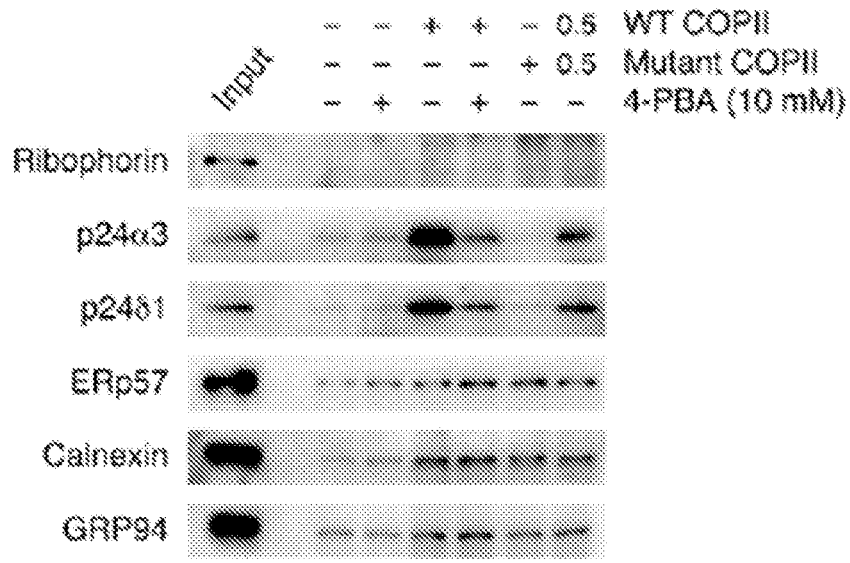
FIG. 4(A) shows reconstituted COPII budding reactions that were performed on permeabilized CHO cells (expressing neither wild-type nor mutant LDL receptor). The lane labeled Input represents 1.1% of the starting membranes used in a budding reaction; all other lanes represent the vesicle product of 100% of the starting membranes. Experiments were performed in triplicate.
Figure 4B:
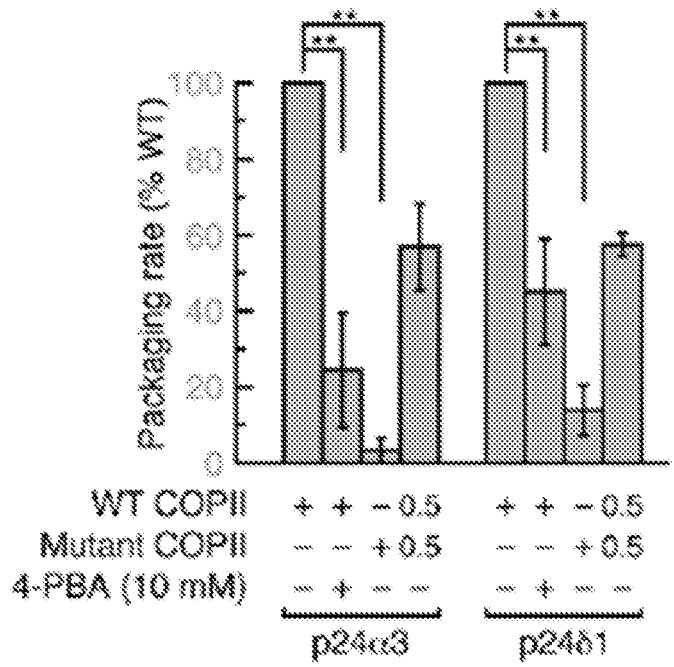
FIG. 4(B) shows a graph showing data in FIG. 4(A), which were corrected as in FIG. 2(D), using the mean values of the packaging rates for Syntaxin 5, Erv46 and Rer1 (n=3; ANOVA test, Bonferroni-Holm post hoc, **$P<0.01$). Bar graphs show mean±s.e.m.
Figure 4C:
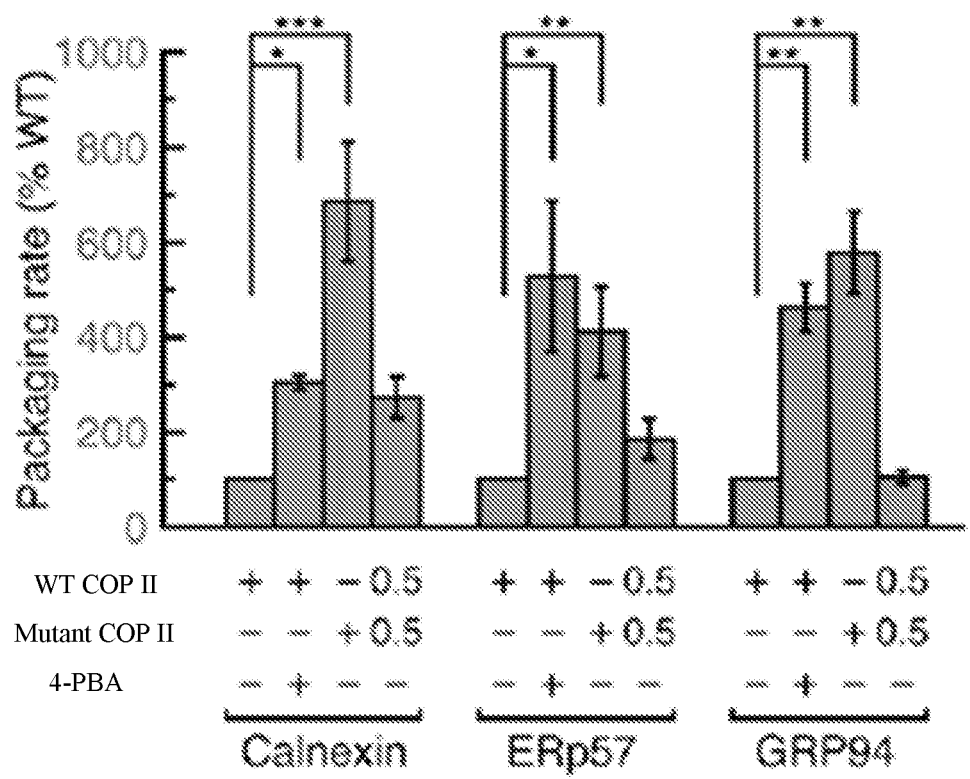
FIG. 4(C) shows a graph depicting packaging rates for Calnexin, ERp57 and GRP94 (n=3; ANOVA test, Bonferroni-Holm post hoc, *$P<0.05$, $P<0.01$ and *$P<0.001$). Bar graphs show mean±s.e.m.

As shown in FIG. 4(A), the packaging of proteins into vesicles budded from parent CHO cells exhibits the same pattern of p24-dependence as from ER stressed cells. Vesicles budded with B-site-mutant COPII are depleted of p24 proteins by a factor of ~8-fold (FIG. 4(B)), yet the same pool of vesicles packages on average 5.5-fold higher levels of resident proteins (FIG. 4(C)). This indicates a ~40-fold purification achieved by the COPII coat. These observations confirm the original finding of stringent exclusion of BiP from yeast COPII vesicles and indicate that ER retention was properly imposed in the permeabilized-cell assay (see Example 4).

Quantification of these data in Table 3 shows that wild-type COPII vesicles package resident proteins at a 5-fold higher rate from ER stressed cells than from ER unstressed cells, whereas the packaging rates of bona fide cargo proteins were essentially the same. In addition to the increased rate of packaging, it is also the case that unfolded protein response (UPR) activation increases resident chaperone concentrations.

The combination of increased levels (see, for example, FIG. 5) and increased packaging rates of resident proteins that were observe in ER stressed cells yields substantial leakage into vesicles that is consistent with the observations of post-ER trafficking of residents and misfolded proteins cited above.

The results of these budding experiments show two general effects concerning resident protein retention in the ER: 1) a constitutive leakage in the UPR-activated cell and 2) the p24-dependent sorting of resident proteins from cargo to impose ER retention as a general property of COPII vesicle budding in ER stressed and ER unstressed cells.

Example 6—Extracellular Secretion of the KDEL-Tagged (SEO ID NO: 3) Resident Chaperone GRP94

This example demonstrates that treatment with 4-PBA resulted in a secretion of ER luminal resident proteins.

Methods

CHO cells expressing G544V-mutant LDL receptor were incubated with increasing concentrations of 4-PBA (0, 5, 10, 20, and 40 mM) for 24 hours at 37° C. The presence of KDEL tagged (SEQ ID NO: 3) luminal chaperone GRP94 inside and outside cells was measured.

Results

Figure 5A:
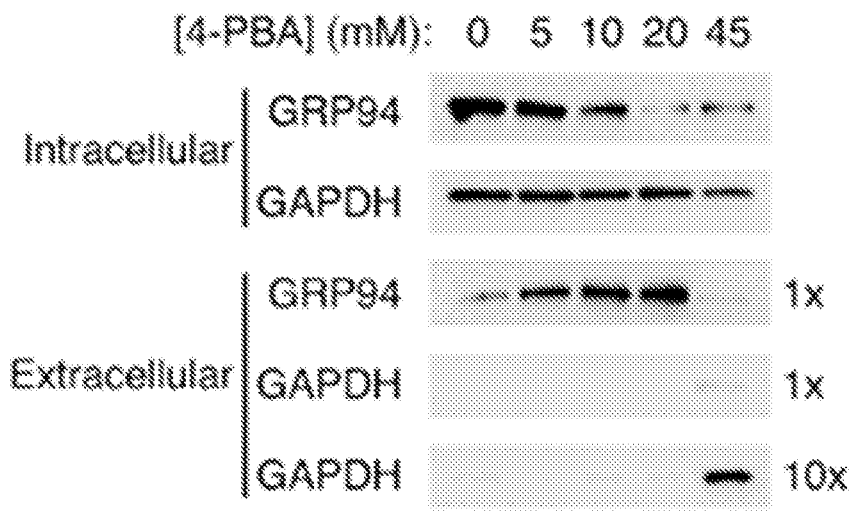
FIG. 5(A) shows CHO cells expressing G544V-mutant LDL receptor that were incubated with increasing concentrations of 4-PBA for 24 hours at 37° C. Extracellular GRP94 in the medium was analyzed directly. The ER trapping of the mutant LDL receptor caused UPR leading to elevated levels of intracellular GRP94 (0 mM 4-PBA lane), and that unfolded protein response (UPR) was attenuated at 10-20 mM 4-PBA.
Figure 5B:
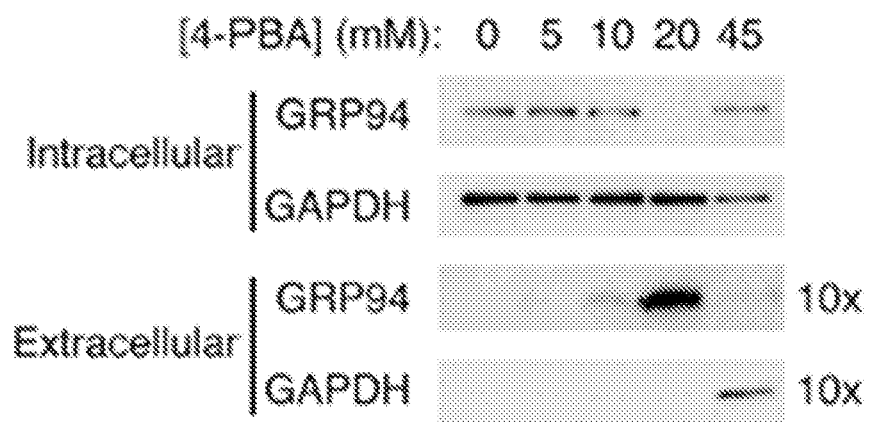
FIG. 5(B) shows GRP94 protein levels in ER unstressed wild-type CHO cells. The blots in FIGS. 5(A)-5(B) show intracellular levels of GRP94 were from equivalent amounts of cells (based on total protein measurement). To detect extracellular GRP94, ten times more sample was loaded than in FIG. 5(A).

Secretion of GRP94 from CHO cells was dose-dependent on 4-PBA and maximal at 20 mM 4-PBA, from both ER stressed and ER unstressed cells (FIGS. 5(A)-5(B), respectively). GRP94 was released by secretion rather than by cell lysis, because the cytosolic marker GAPDH was absent from the extracellular sample. At the highest concentration, 45 mM 4-PBA, cell lysis was detected and the cells lost all ability to secrete GRP94.

The profile of GRP94 secretion from ER stressed CHO cells closely matches that of the restoration of trafficking of the mutant LDL receptor (compare FIGS. 3(B) and 5(A)). Additionally, the 4-PBA-dependent secretion of GRP94 was also observed from ER unstressed cells, even though significantly lower levels of GRP94 were present intracellularly at the outset of the assay (compare top rows in FIGS. 5(A) and 5(B)).

Intracellular GRP94 levels in ER stressed cells were reduced over time as incubation with 4-PBA attenuated the UPR. As such, increasing concentration of 4-PBA (a treatment that lowers rather than raises UPR signaling levels) causes the secretion of GRP94.

In view of the previous results, this data shows that 4-PBA targets COM to reduce the fidelity of ER retention, the dose-response profiles of GRP94 secretion from ER stressed and ER unstressed cells are different (FIGS. 5(A)-5(B)), ER stressed cells secrete GRP94 in the absence of 4-PBA (albeit at low levels), and there is a linear relationship between 4-PBA concentration and GRP94 secretion for ER stressed cells (FIG. 5(A)).

Since the KDEL retrieval system is saturable, these results also indicate that resident protein leakage into COPII vesicles in ER stressed cells, even in the absence of 4-PBA, delivers KDEL ligands to post-ER membranes at levels that approach or just exceed the capacity of the retrieval system.

The profile of GRP94 secretion from ER unstressed cells is a step response; only at high concentrations of 4-PBA does resident leakage seem to exceed a threshold level to cause saturation of the KDEL retrieval system (FIG. 5(B)). The results show that protein sorting by COPII maintains resident protein leakage rates substantially below the threshold level, to render a useful dynamic range to the KDEL retrieval system under normal conditions.

The results also show that forward transport of the KDEL receptor substantially exceeds that of KDEL ligands, through the combination of receptor concentration and ligand depletion (FIG. 4) in COPII vesicles. This indicates that ER residency is stringently imposed in ER unstressed cells by synergy of the COPII dependent retention and KDEL-dependent retrieval mechanisms.

Additionally, the results show that 4-PBA caused the extracellular secretion of GRP94, in addition to restoring the trafficking of misfolded mutant LDL receptor, thereby phenocopying p24 mutant yeast and worms. The results indicate that ER residency relies on the superposition of the retention and retrieval processes. While the experiments focus on KDEL-mediated retrieval, it is likely that additional retrieval systems, e.g., involving Rer1 and Erv41-Erv46, will also be supported by COPII-dependent retention.

The saturation of the KDEL system (see FIG. 5(A)) indicates that it is relevant to the mechanism by which 4-PBA restores trafficking of misfolded LDL receptor. If escaped receptor molecules can be bound by chaperones such as BiP and retrieved to the ER via the KDEL receptor, then restoration of mutant LDL receptor trafficking by 4-PBA may involve the combination of enhanced ER exit (FIG. 3) and reduced retrieval upon saturation of the KDEL system.

These results demonstrate that the compositions of the present technology are useful in increasing extracellular secretion of GRP94 (and thus GRP94:antigen complexes) in ER stressed cells (such as cancer cells). Accordingly, the compositions disclosed herein are useful in methods for enhancing cancer or viral immunotherapy.

Example 7—Sec24 Protein as a Target of 4-PBA

This example demonstrates that 4-PBA targets the COPII coat.

Methods

As a further test of COPII protein as a cellular target of 4-PBA, a series of 4-PBA analogs (FIG. 8) were tested for their ability to restore trafficking of the mutant LDL receptor in the cell-based assay (FIGS. 6(A)-6(D)) and their binding affinity for Sec24 protein (FIGS. 6(E)-6(G)).

Trafficking Assay:

CHO cells expressing G544V-mutant LDL receptor were incubated with the indicated concentrations of 4-PBA analogs for 2 hours at 37° C. Cell lysates were analyzed by immunoblotting for the appearance of 160 kDa mature glycosylated LDL receptor (labeling indicates the position of 160 kDa mature glycosylated and 120 kDa precursor forms of LDL receptor). Gamma correction was applied to the immunoblot images.

Binding Assay:

A competition binding assay based on fluorescence polarization that measures the affinity of 4-PBA analogs according to their ability to displace a fluorescent tracer peptide from Sec24a. The tracer was a modified DxE export sequence of VSV G protein, which binds to the B site, hence the assay signal reports on specific binding to this site.

The results of the two assays are shown in FIG. 6(H).

Results

The potency with which the 4-PBA analogs restored trafficking of mutant LDL receptor increases in rank order of affinity for COPII protein. These results, together with the crystallographic observations (see Examples 1 and 2) and the vesicle budding experiments (see Examples 1 and 2) provide multiple independent lines of evidence that 4-PBA targets the COPII coat.

Accordingly, the compositions of the present technology are useful in methods for modifying the trafficking of peptides and/or proteins from the ER.

Example 8—Extracellular Secretion of the KDEL-Tagged (SEQ ID NO: 3) Resident Chaperone GRP94 in 4-PBA-Treated Cancer Cells This example demonstrates that treatment with 4-PBA will result in increased extracellular GRP94 secretion in cancer cell lines.

Methods

Any suitable cancer cell line may be utilized in the present example. Breast cancer cells (e.g., MCF7), prostate cancer cells (e.g., PC-3), renal cancer cells (e.g., TK-10), ovarian cancer cells (e.g., SK-OV3), melanoma cells (e.g., SK-MEL-2), CNS cancer cells (e.g., SF-268), colon cancer cells (e.g., COLO 205), leukemia cells (e.g., K-562) and NSCLC cells (e.g., NCI-H460), which either express G544V-mutant LDL receptor construct or an empty vector, will be incubated with increasing concentrations of 4-PBA (0, 5, 10, 20, and 40 mM) for 24 hours at 37° C. The presence of KDEL tagged (SEQ ID NO: 3) luminal chaperone GRP94 inside and outside cells will be measured by Western Blot. In order to detect MHC class I precursor peptides chaperoned by GRP94, peptides will be stripped from the GRP94 protein isolated from the extracellular fraction using the methods described in Ishii T et al., *J. Immunol.* 162: 1303-1309 (1999) and will be analyzed via mass spectrometry. Eluted peptides will be pulsed onto target cells and functional activity will be assessed in a CTL assay. See Binder et al., *J Immunol* 179: 7254-7261 (2007).

Results

It is anticipated that one or more of the cancer cell lines treated with 4-PBA will show increased extracellular GRP94 levels compared to that observed in the untreated cancer cell lines. It is expected that one or more of the 4-PBA-treated cancer cells that are under ER stress will show higher levels of GRP94 secretion compared to 4-PBA-treated cancer cells that are not under ER stress. It is also anticipated that the secreted GRP94 from the one or more 4-PBA treated cancer cell lines will be associated with tumor neoantigens that will be detectable by mass spectrometry and CTL assay.

These results demonstrate that the compositions of the present technology are useful in increasing extracellular secretion of GRP94 (and thus GRP94:antigen complexes) in cells. Accordingly, the compositions disclosed herein are useful in methods for enhancing cancer or viral immunotherapy.

Example 9—Therapeutic Effects of 4-PBA in B16-F10 Tumor Mice

This example demonstrates that treatment with 4-PBA will reduce tumor growth in a murine cancer model.

Methods

Survival Experiments.

In all experiments, animals are assigned to various experimental groups at random (placebo, 4-PBA only, anti-CTLA-4 only, or 4-PBA+anti-CTLA-4). For survival studies, sample sizes of 10-15 mice per group are used. Survival analyses is performed using the log-rank test. For the B16-F10 model, tumors are implanted by injection of $1 \times 10^5$ cells in the right flank intradermally (i.d.) on day 0 and $5 \times 10^4$ cells in the left flank on day 4. On days 7, 10, 13, and 16, the mice are treated with different concentrations of 4-PBA (e.g., 1 μM-400 mM) and/or 100 μg of i.p. anti-CTLA-4 antibody. Control groups receive a corresponding dose of isotype antibody i.p. and PBS. For depletion of immune cells, mice are injected i.p. with 500 μg of monoclonal antibodies to CD8+, CD4+, NK1.1 or IFNγ one day before and two days after tumor challenge, followed by injection of 250 μg every 5 days throughout the experiment.

Tumor-Infiltrating Lymphocyte Assay.

B16-F10 tumors are implanted by injection of $2 \times 10^5$ B16-F10 cells in the right flank i.d. on day 0 and $2 \times 10^5$ cells in the left flank on day 4. On days 7, 10, and 13, the mice are treated with different concentrations of 4-PBA (e.g., 1 μM-400 mM) and/or 100 μg of i.p. anti-CTLA-4 antibody. On day 15, the mice are sacrificed and tumors and tumor-draining lymph nodes are removed using forceps and surgical scissors and weighed. Tumors from each group are minced with scissors prior to incubation with 1.67 Wünsch U/mL Liberase and 0.2 mg/mL DNase for 30 minutes at 37° C. Tumors are homogenized by repeated pipetting and filtered through a 70-μm nylon filter. Cell suspensions are washed once with complete RPMI and purified on a Ficoll gradient to eliminate dead cells.

Results

It is anticipated that B16-F10 tumor bearing mice treated with either 4-PBA or anti-CTLA-4 antibody will show an increase in survival, an increase in tumor infiltration and/or a reduction in tumor size compared to the untreated placebo group. It is also anticipated that animals receiving both 4-PBA and anti-CTLA-4 will exhibit a synergistic increase in survival and/or tumor infiltration, and/or a synergistic reduction in tumor growth compared to that observed with either 4-PBA or anti-CTLA-4 antibody alone. Accordingly, the compositions disclosed herein are useful in methods for treating cancer in a subject in need thereof.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

What is claimed is:

1. A method for enhancing responsiveness of a subject infected with a virus to viral immunotherapy comprising administering to the subject 4-phenylbutyrate (4-PBA), 4-(4-methoxyphenyl)butyrate (methoxy-PBA), 3-phenylpropionate (3-PPA), 5-phenylvalerate (5-PVA), 3-(4-hydroxyphenyl)propionate (hydroxy-PPA), 4-(4-hydroxyphenyl) butyrate (hydroxy-PBA), 4-(4-tolyl) butyrate (tolyl-BA), or a compound of Formula I:

(Formula I)

wherein $R^1$ is H, $C_1$-$C_3$ alkyl, $C_1$-$C_3$ alkoxy, hydroxyl, thiol, $C_1$-$C_3$ alkylthio, —S(O)$R^2$, —S(O)$_2R^3$, or —S(O)$_2OR^4$; $R^2$, $R^3$, and $R^4$ are independently $C_1$-$C_3$ alkyl; and n is 2, 3, or 4, in an amount that is effective to elevate secretion of GRP94/viral antigen complexes in the subject compared to that in the subject prior to administration; and one or more immune checkpoint inhibitors selected from the group consisting of ipilimumab, pembrolizumab, nivolumab, atezolizumab, avelumab, durvalumab, pidilizumab, AMP-224, MDX-1105, arelumab, tremelimumab, IMP321, MGA271, BMS-986016, lirilumab, urelumab, PF-05082566, IPH2101, MEDI-6469, CP-870,893, Mogamulizumab, Varlilumab, Galiximab, AMP-514, and AUNP 12.

2. The method of claim 1, wherein the virus is selected from the group consisting of human immunodeficiency virus (HIV), herpes simplex virus (HSV), influenza virus, EBV, Ebola virus, chicken pox virus, Hepatitis B virus, Hepatitis C virus, HPV, rubeola virus, rubulavirus, rubella virus, poliovirus, Rous Sarcoma Virus, rabies virus, and rotavirus.

3. The method of claim 1, comprising separately, sequentially or simultaneously administering one or more immune system stimulators selected from the group consisting of IL-2, IL-15, IL-15/IL-15RA complex, IL-18, IL-12, CD28, inducible costimulatory (ICOS), CD40, CD30, CD27, OX-40, 4-1BB, and a granulocyte macrophage colony-stimulating factor (GM-CSF).

4. The method of claim 1, further comprising administering an effective amount of an adjuvant.

5. The method of claim 1, wherein 4-PBA, methoxy-PBA, 3-PPA, 5-PVA, hydroxy-PPA, hydroxy-PBA, tolyl-BA, or the compound of Formula I is administered orally, topically, intranasally, systemically, intravenously, subcutaneously, intraperitoneally, intradermally, intraocularly, iontophoretically, transmucosally, or intramuscularly.

* * * * *